United States Patent [19]
Szoka, Jr. et al.

[11] Patent Number: 5,811,406
[45] Date of Patent: Sep. 22, 1998

[54] DRY POWDER FORMULATIONS OF POLYNUCLEOTIDE COMPLEXES

[75] Inventors: Francis C. Szoka, Jr., San Francisco, Calif.; Alain Rolland, The Woodlands, Tex.; Jinkang Wang, San Francisco, Calif.

[73] Assignee: Regents of the University of California, Oakland, Calif.

[21] Appl. No.: 482,254

[22] Filed: Jun. 9, 1995

Related U.S. Application Data

[63] Continuation-in-part of Ser. No. 482,110, Jun. 7, 1995, and Ser. No. 485,430, Jun. 7, 1995.

[51] Int. Cl.⁶ .................................................. A61K 48/00
[52] U.S. Cl. ......................... 514/44; 536/23.1; 536/24.5; 435/172.3; 424/450
[58] Field of Search ............................. 514/44; 536/23.1, 536/24.5; 424/450; 435/172.3

[56] References Cited

U.S. PATENT DOCUMENTS 4,766,046  8/1988  Abra et al. ............................... 424/450

OTHER PUBLICATIONS

Mennino, et al. 1988 Biotechniques vol. 6. No. 7. pp. 682–690 "Lipsome Mediated Gene Transfer".

Gura, T. 1995. Science vol. 270 pp. 575–577. "Antisense His Growing Pains".

Orkin, et al. Dec. 7, 1995. "Report and Recommendations of The Panel to Assess The NIH Investment in Research on Gene Therapy".

Primary Examiner—James Ketter
Assistant Examiner—Irem Yucel
Attorney, Agent, or Firm—Crosby, Heafey, Roach & May

[57] ABSTRACT

Polynucleotide complexes are stabilized by adding a cryoprotectant compound and lyophilizing the resulting formulation. The lyophilized formulations are milled or sieved into a dry powder formulation which may be used to deliver the polynucleotide complex. Delivery of the polynucleotide to a desired cell tissue is accomplished by contacting the tissue with the powder to rehydrate it. In a preferred embodiment, a dry powder formulation is used to transfer genetic information to the cells of the respiratory tract.

19 Claims, 23 Drawing Sheets

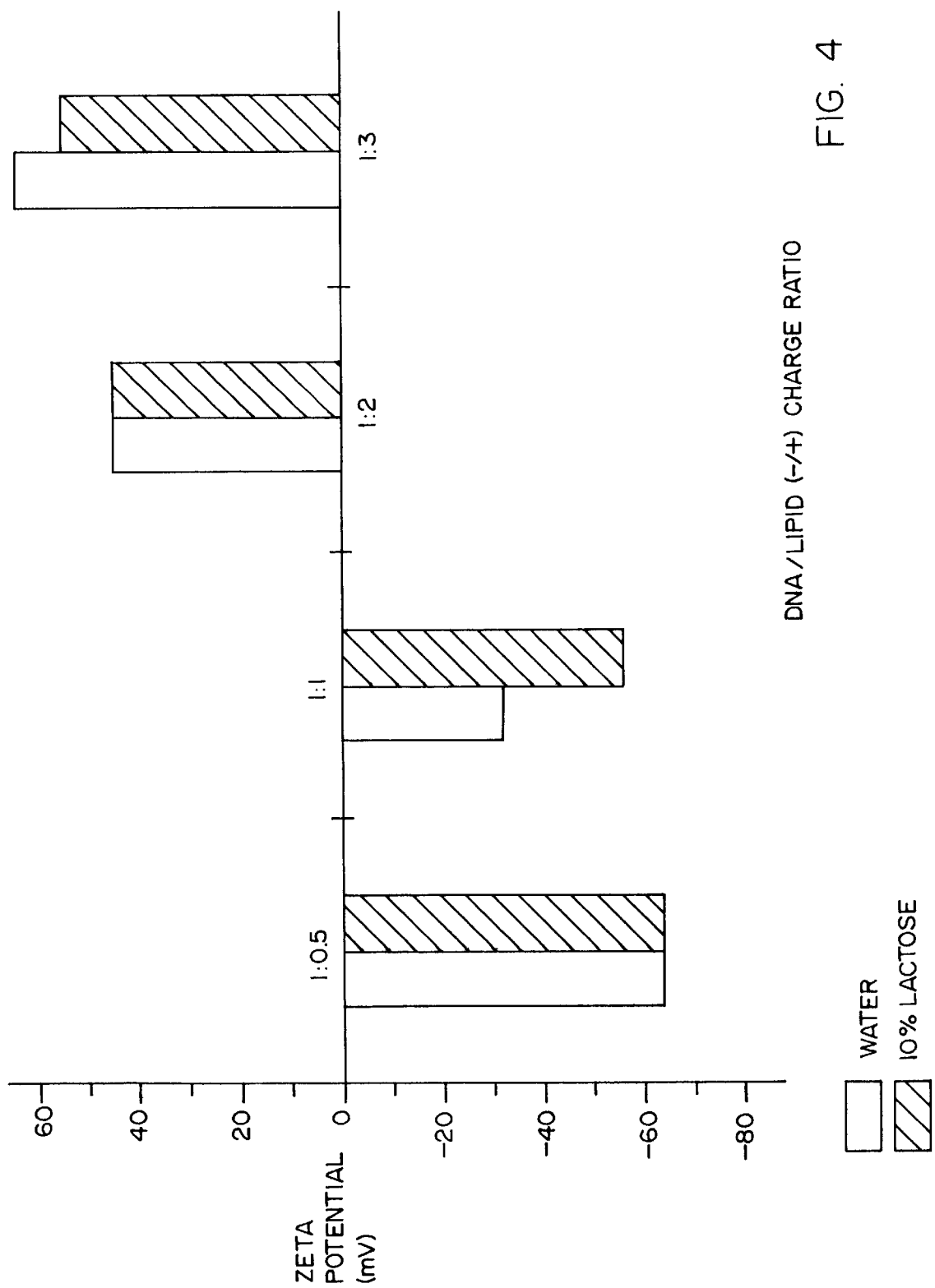

1% AGARORE GEL ELECTROPHORESIS OF DNA/LIPID COMPLEX IN THE PRESENCE OF 10% LACTOSE:

BEFORE LYOPHILIZATION

LANE 1: 1:2 -/+, DOTMA:DOPE, 55:45 mol%, 100 nm
LANE 2: 1:2 -/+, DOTMA:DOPE, 40:60 mol%, 100 nm
LANE 3: 1:3 -/+, DOTMA:DOPE, 40:60 mol%, 100 nm
LANE 4: 1:0.5 -/+, DOTMA:DOPE, 55:45 mol%, 100 nm
LANE 5: FREE DNA
LANE 6: MOLECULAR STANDARD

AFTER LYOPHILIZATION AND REHYDRATION

LANE 7: 1:2 -/+, DOTMA:DOPE, 55:45 mol%, 100 nm
LANE 8: 1:2 -/+, DOTMA:DOPE, 40:60 mol%, 100 nm
LANE 9: 1:3 -/+, DOTMA:DOPE, 40:60 mol%, 100 nm
LANE 10: 1:0.5 -/+, DOTMA:DOPE, 55:45 mol%, 100 nm

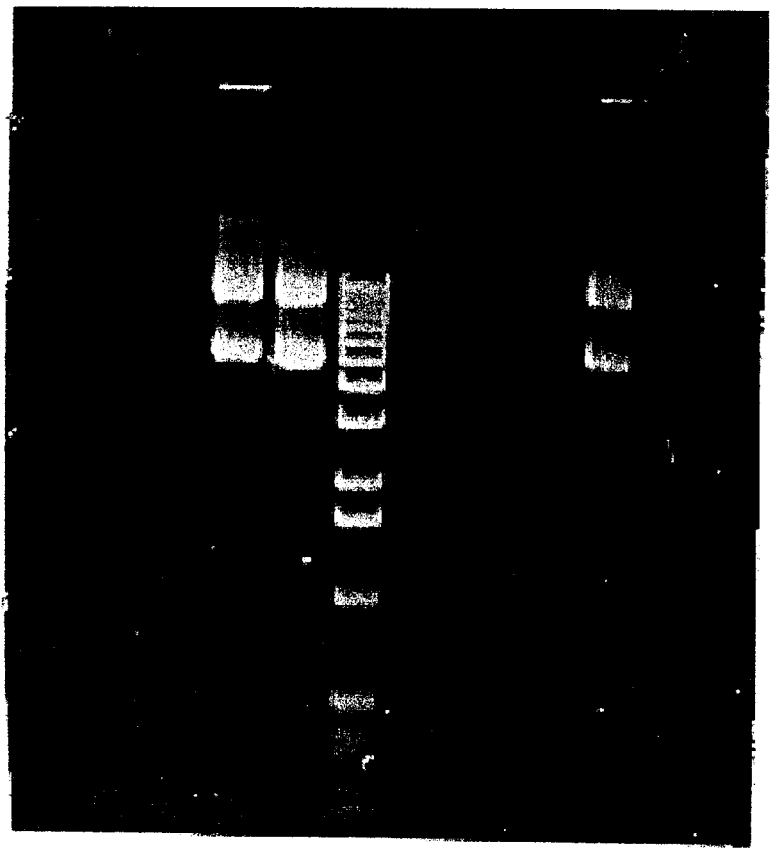

FIG. 5

| 0.5 | 1 | 2 |
|---|---|---|
| 1.26043192 | 0.94252446 | 1.7548417 |
| 1.73700788 | 1.33328768 | 1.63319055 |
| 1.47497478 | 3.42788914 | 4.45416501 |
|  |  |  |
|  |  |  |
| 0.0994683 | 0.66333021 | 1.19361776 |
| 2.6151192 | 9.25876445 | 10.2815366 |
| 1.89352143 | 4.493411 | 4.83866979 |
|  |  |  |
|  |  |  |
| 3.10129932 | 7.10040842 | 15.7079412 |
| 2.81220453 | 15.0057574 | 15.5783623 |

|  | 0.5 | 1 | 2 |
|---|---|---|---|
| −20/1.195/2.5 | 5.04734977 | 7.16577876 | 14.8179102 |
| −20/1.195/7.5 | 9.95183959 | 10.6275075 | 11.4653052 |
| −20/1.195/2.5 | 4.70971109 | 9.6597626 | 14.9210362 |
| −20/1.195/7.5 | 4.47827902 | 12.0081383 | 17.1636935 |
| −20/0.797/2.5 | 7.73486319 | 5.08070022 | 10.3487906 |
| −20/0.797/7.5 | 3.59865556 | 10.5523598 | 13.6480229 |
| −20/0.797/2.5 | 4.62408195 | 6.13467108 | 12.2034914 |
| −20/0.797/7.5 | 2.80149694 | 10.8198627 | 10.914942 |
| −20/1.195/0 | 0.06094907 | 0.04002715 | 0.01966328 |
| −20/0.797/0 | 0.06084848 | 0.04037617 | 0.04013559 |
| CONTROL 1.195 | 1.18464231 | 5.91949311 | 13.8337681 |
| CONTROL 0.797 | 4.72637187 | 12.1243006 | 10.8052363 |

|  | 0.5 | 1 | 2 |
|---|---|---|---|
| -80/1.195/2.5 | 4.46501541 | 11.3499567 | 19.994397 |
| -80/1.195/7.5 | 4.9376138 | 15.4666962 | 16.8378859 |
| -80/1.195/2.5 | 1.52134342 | 5.06795157 | 8.26589036 |
| -80/1.195/7.5 | 3.53669702 | 14.2612373 | 14.0382344 |
| -80/0.797/2.5 | 6.32844201 | 9.1674627 | 15.375282 |
| -80/0.797/7.5 | 5.76481641 | 11.4539779 | 11.6737735 |
| -80/0.797/2.5 | 4.43209811 | 8.9151476 | 20.9330925 |
| -80/0.797/7.5 | 14.5601947 | 21.1112751 | 30.89712 |
| -80/1.195/0 | 0.02995289 | 0.06094907 | 0.0416026 |
| -80/0.797/0 | 0 | 0.04013559 | 0.13544231 |
| CONTROL 1.195 | 1.18464231 | 5.91949511 | 13.8337681 |
| CONTROL 0.797 | 4.72637187 | 12.1243008 | 10.8052363 |

R¹ = (CH₂)nCH₃ n = 2 to 30, 1 to 6 unstaurated bonds or iso CH₃ groups.

DRY POWDER FORMULATIONS OF POLYNUCLEOTIDE COMPLEXES

RELATION TO OTHER APPLICATIONS

This application is a continuation-in-part of U.S. application Ser. No. 08/482,110 filed Jun. 7, 1995 and U.S. application Ser. No. 08/485,430 filed Jun. 7, 1995.

ACKNOWLEDGEMENT OF GOVERNMENT SUPPORT

The government has rights in this invention pursuant to Grant No. GM-30163 awarded by the National Institutes of Health.

BACKGROUND ART

Molecular biologists have identified the chromosomal defects in a large number of human hereditary diseases, raising the prospects for cures using gene therapy. This emerging branch of medicine aims to correct genetic defects by transferring cloned and functionally active genes into the afflicted cells. Several systems and polymers suitable for the delivery of polynucleotides are known in the art. In addition, gene therapy may be useful to deliver therapeutic genes to treat various acquired and infectious diseases, autoimmune diseases and cancer.

Despite the usefulness of polynucleotide delivery systems, such systems are metastable and typically exhibit a decrease in activity when left in solution for longer than a few hours. For example, conventional cationic-lipid mediated gene transfer requires that the plasmid DNA and the cationic lipid be separately maintained and only mixed immediately prior to the gene transfer. Current attempts to stabilize polynucleotide complexes comprise speed-vac or precipitation methods, but they do not maintain activity over suitable time periods. Attempts to store polynucleotides in salt solutions lead to a loss of supercoil structure. If gene therapy protocols are to become widely used it will be necessary to have a stable and reproducible system for maintaining activity. This is of particular importance to pharmaceutical and commercial uses. Accordingly, there remains a need for means to stably maintain polynucleotide compositions for extended periods of time. The present invention satisfies this and other needs.

SUMMARY OF THE INVENTION

The invention comprises a method of stabilizing polynucleotide complexes by adding a cryoprotectant compound and lyophilizing the resulting formulation. Cryoprotectant compounds comprise carbohydrates, preferably lactose and sucrose, but also glucose, maltodextrins, mannitol, sorbitol, trehalose, and others. Betaines prolines, and other amino acids may also be useful. Preferably, the invention comprises DNA complexes cryoprotected with lactose at concentrations of about 1.25% to about 10% (w/vol). Conventional buffers may also be added to the mixture. The invention also comprises the lyophilized mixtures.

The lyophilized formulations may be stored for extended periods of time and then rehydrated prior to use. In an alternative embodiment, the lyophilized formulations may be milled or sieved into a dry powder formulation which may be used to deliver the polynucleotide complex. Once the powder contacts the desired tissue, it rehydrates, allowing delivery of the polynucleotide complex. In a preferred embodiment, a dry powder formulation is used to induce genetic modification of a patient's lung tissue.

BRIEF DESCRIPTION OF THE DRAWINGS

FIG. 4 illustrates the effect of cryoprotectant on the zeta potential of lipid-polynucleotide complexes.

FIG. 5 is a graphical representation of gel electrophoresis results indicating the effect of lyophillization on complexation between lipid and polynucleotide.

DETAILED DESCRIPTION OF THE DRAWINGS

Figure 1:
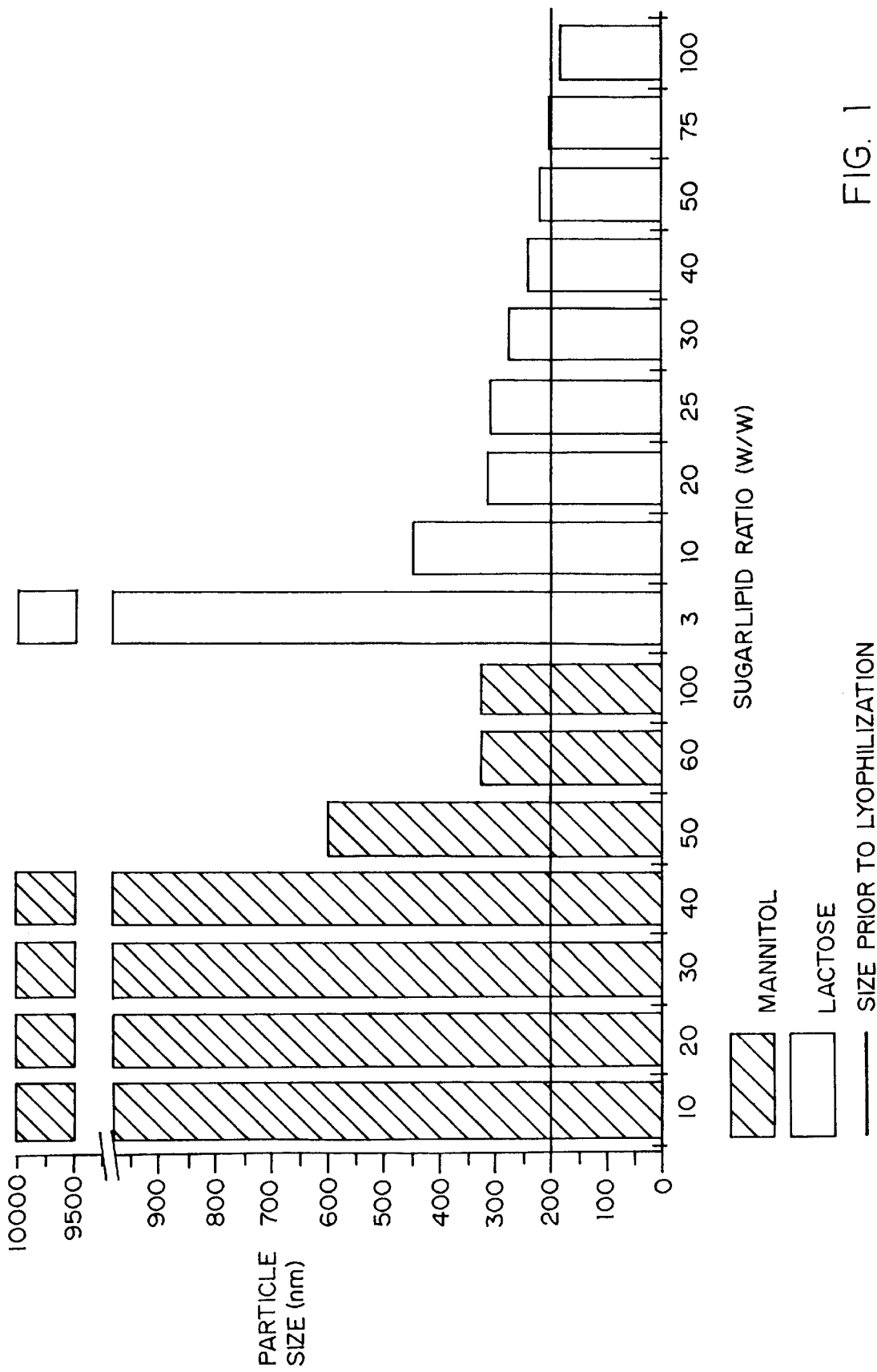
FIG. 1 shows the effect of rehydration on the particle size distribution of lipid-polynucleotide complexes at varying concentrations of mannitol and lactose.

The invention comprises stabilizing polynucleotide complexes by adding a cryoprotectant and lyophilizing the resulting mixture. Cryoprotectant compounds comprise carbohydrates, preferably lactose and sucrose, but also glucose, maltodextrins, mannitol, sorbitol, trehalose, and others. It is believed the hydroxyl groups of the carbohydrates form hydrogen bonds with the polynucleotide complexes, displacing water and stabilizing the complexes. Useful ranges of cryoprotectant range from about 1.25% to about 10%, and particularly from 5–10%. Other suitable cryoprotectants include amino acids such as betaines and prolines that exhibit this hydrogen bonding stabilization effect.

A wide variety of polynucleotide complexes may be stabilized with the lyophillization techniques of this invention. The polynucleotide may be a single-stranded DNA or RNA, or a double-stranded DNA or DNA-RNA hybrid. Triple- or quadruple-stranded polynucleotides with therapeutic value are also contemplated to be within the scope of this invention. Examples of double-stranded DNA include structural genes, genes including operator control and termination regions, and self-replicating systems such as plasmid DNA, among others.

Single-stranded polynucleotides or "therapeutic strands" include antisense polynucleotides (DNA and RNA), ribozymes and triplex-forming oligonucleotides. In order to have prolonged activity, the therapeutic strand preferably has as some or all of its nucleotide linkages stabilized as non-phosphodiester linkages. Such linkages include, for example, phosphorothioate, phosphorodithioate, phosphoroselenate, or O-alkyl phosphotriester linkages wherein the alkyl group is methyl or ethyl, among others.

For these single-stranded polynucleotides, it may be preferable to prepare the complementary or "linker strand" to the therapeutic strand as part of the administered composition. The linker strand is usually synthesized with a phosphodiester linkage so that it is degraded after entering the cell. The "linker strand" may be a separate strand, or it may be covalently attached to or a mere extension of the therapeutic strand so that the therapeutic strand essentially doubles back and hybridizes to itself. Alternatively, the linker strand may have a number of arms that are complementary so that it hybridizes to a plurality of polynucleotide strands.

The linker strand may also have functionalities on the 3' or 5' end or on the carbohydrate or backbone of the linker that serve as functional components to enhance the activity of the therapeutic strand. For example, the phosphodiester linker strand may contain a targeting ligand such as a folate derivative that permits recognition and internalization into the target cells. If the linker is attached to its complementary therapeutic strand that is composed of degradation-resistant linkages, the duplex would be internalized. Once inside the cell, the linker will be degraded, thereby releasing the therapeutic strand. In this manner, the therapeutic strand will have no additional functionalities attached and its function will not be impeded by non-essential moieties. This strategy can be applied to any antisense, ribozyme or triplex-forming polynucleotide and it is used to deliver anti-viral, anti-bacterial, anti-neoplastic, anti-inflammatory, anti-proliferative, anti-receptor blocking or anti-transport polynucleotides, and the like.

A separate linker strand may be synthesized to have the direct complementary sequence to the therapeutic strand and hybridize to it in a one-on-one fashion. Alternatively, the linker strand may be constructed so that the 5' region of the linker strand hybridizes to the 5' region of the therapeutic strand, and the 3' region of the linker strand hybridizes to the 3' region of the therapeutic strand to form a concatenate of the following structure.

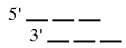

This concatenate has the advantage that the apparent molecular weight of the therapeutic nucleic acids is increased and its pharmacokinetic properties and targeting ligand:therapeutic oligonucleotide ratio can be adjusted to achieve the optimal therapeutic effect. The linker strand may also be branched and able to hybridize to more than one copy of the polynucleotide. Other strategies may be employed to deliver different polynucleotides concomitantly. This would allow multiple genes to be delivered as part of a single treatment regimen.

The polynucleotide complex may comprise naked polynucleotide such as plasmid DNA, multiple copies of the polynucleotide or different polynucleotides, or may comprise a polynucleotide associated with a peptide, a lipid including cationic lipids, a liposome or lipidic particle, a polycation such as polylysine, a branched, three-dimensional polycation such as a dendrimer, a carbohydrate or other compounds that facilitate gene transfer. Examples of useful polynucleotide compositions are found in U.S. patent applications Ser. No. 08/092,200, filed Jul. 14, 1992, and Ser. No. 07/913,669, filed Jul. 14, 1993, which are hereby incorporated in their entirety by reference thereto.

Results

A 1:1 (w/w) liposome formulation containing the cationic lipid n-[1-(2,3-dioleyloxy)propyl]-N,N,N-trimethylammonium chloride [DOTMA] (obtained from Syntex Inc. (U.S.A.)) and dioleoyl phosphatidylethanolamine (DOPE) was prepared by rehydration of a lipid film with subsequent extrusion under pressure using a 100 nm pore size polycarbonate membrane. Cryoprotectant, lipid and plasmid DNA, containing a CMV promoter and a β-galactosidase (CMV— gal) or chloroamphenicol acetyl transferase (CMV-CAT) reporter gene were mixed together under defined conditions to produce a 1:10:X (w:w:w) of pDNA/lipid/cryoprotectant formulation at a constant pDNA concentration of 250 μg/ml in a final volume of 1 ml, where X was 30, 100, 200, 250, 300, 500, 600, 750 and 100. This corresponds to a DNA:lipid charge ratio of 1:2. The cryoprotectants used were mannitol and lactose. The formulations were lyophillized using a programmable tray dryer (FTS Systems) at a product eutectic temperature of -30° C. The lyophilized formulations were rehydrated at room temperature with water to a pDNA concentration of 250 μg/ml. After 30 minutes, the physicochemical properties of the lipid-pDNA complexes was determined by particle size analysis (Coulter N4MD), doppler electrophoretic light scattering (Coulter Delsa 440) and 1 % agarose gel electrophoresis.

For in vitro studies, transfection efficiency of the pDNA-lipid-cryoprotectant formulations was studied on a variety of cell lines. HIG-82 (rabbit synoviocytes), $C_2$ $C_{12}$ (mouse myoblasts) and HepG2 (human liver hepatoblastoma) cells were grown in F-12 Ham's, Dulbecco's Modified and in minimum essential Eagle's media (Gibco), respectively. All were supplemented with 10% fetal bovine serum (Gibco). Transfection was performed in the presence of serum containing media in 24-well plates at 40–60% cell density with 2 μg of pDNA per well. Cells were harvested and analyzed after 48 hours. A chemiluminescent reporter assay was performed according to TROPIX (Galacto-light ) specifications. The percentage of β-galactosidase (LacZ) positive cells was determined by Commasie Blue protein assay. Relative light units (RLU) per μg of total protein and percentage of LacZ positive cells were used to assess transfection efficiency.

Figure 2:
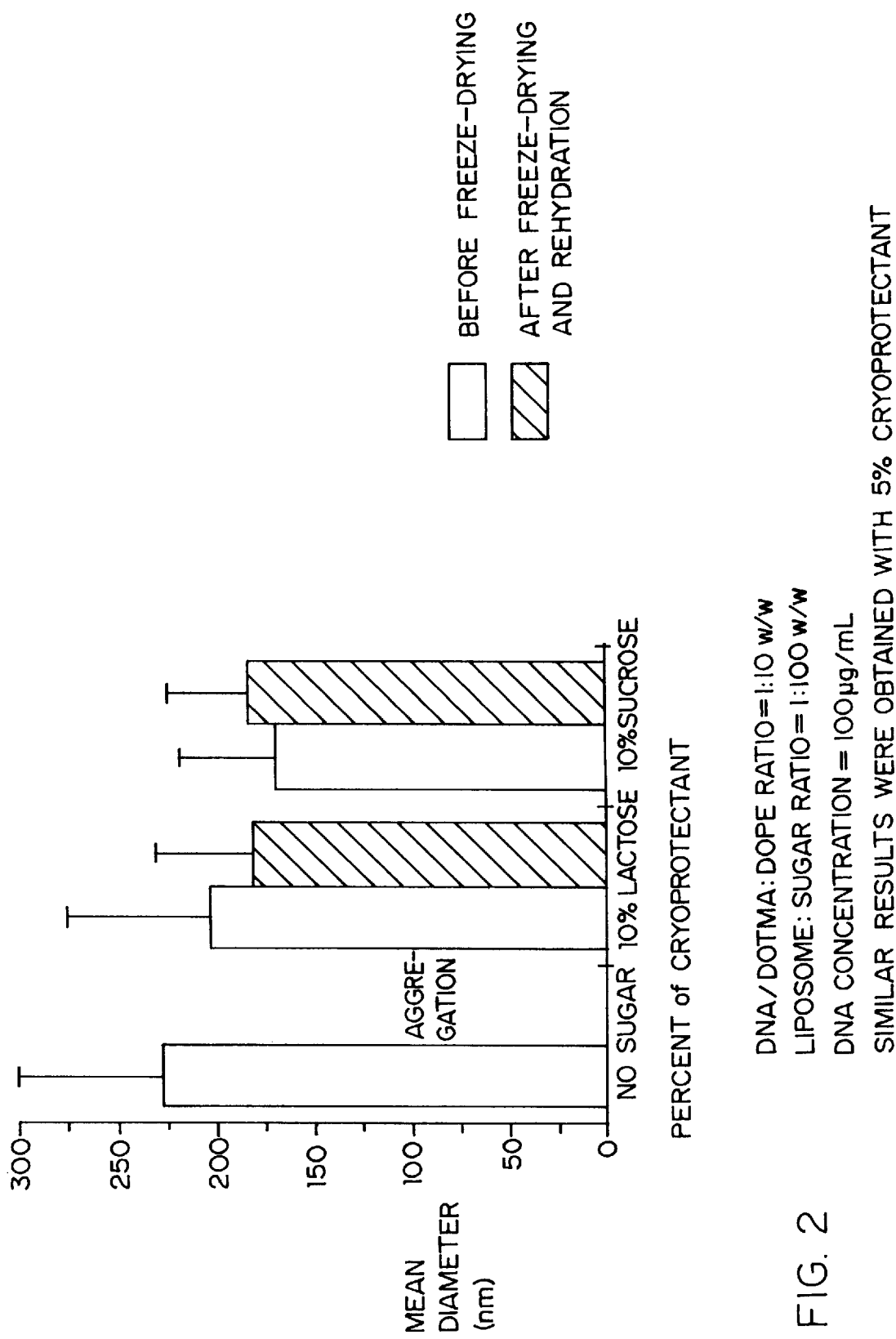
FIG. 2 compares the particle size distribution of lipid-polynucleotide complexes before lyophilization and after rehydration with and without cryoprotectant.

FIG. 1 shows the effect of rehydration on the particle size distribution of lipid-pDNA complexes at varying concentrations of mannitol and lactose. At cryprotectant:lipid ratios of 40:1 to 100:1 (corresponding to 4% and 10% formulations), complexes protected with lactose exhibit similar particle size distribution to non-lyophillized lipid-pDNA complexes. The complexes protected with mannitol exhibit larger particle size distributions. As shown in FIG. 2, lipid-pDNA complexes lyophillized without a cryoprotectant aggregate while lipid-pDNA complexes protected with lactose or sucrose do not aggregate following rehydration and exhibit particles size distributions substantially the same as before lyophillization.

Figure 3:
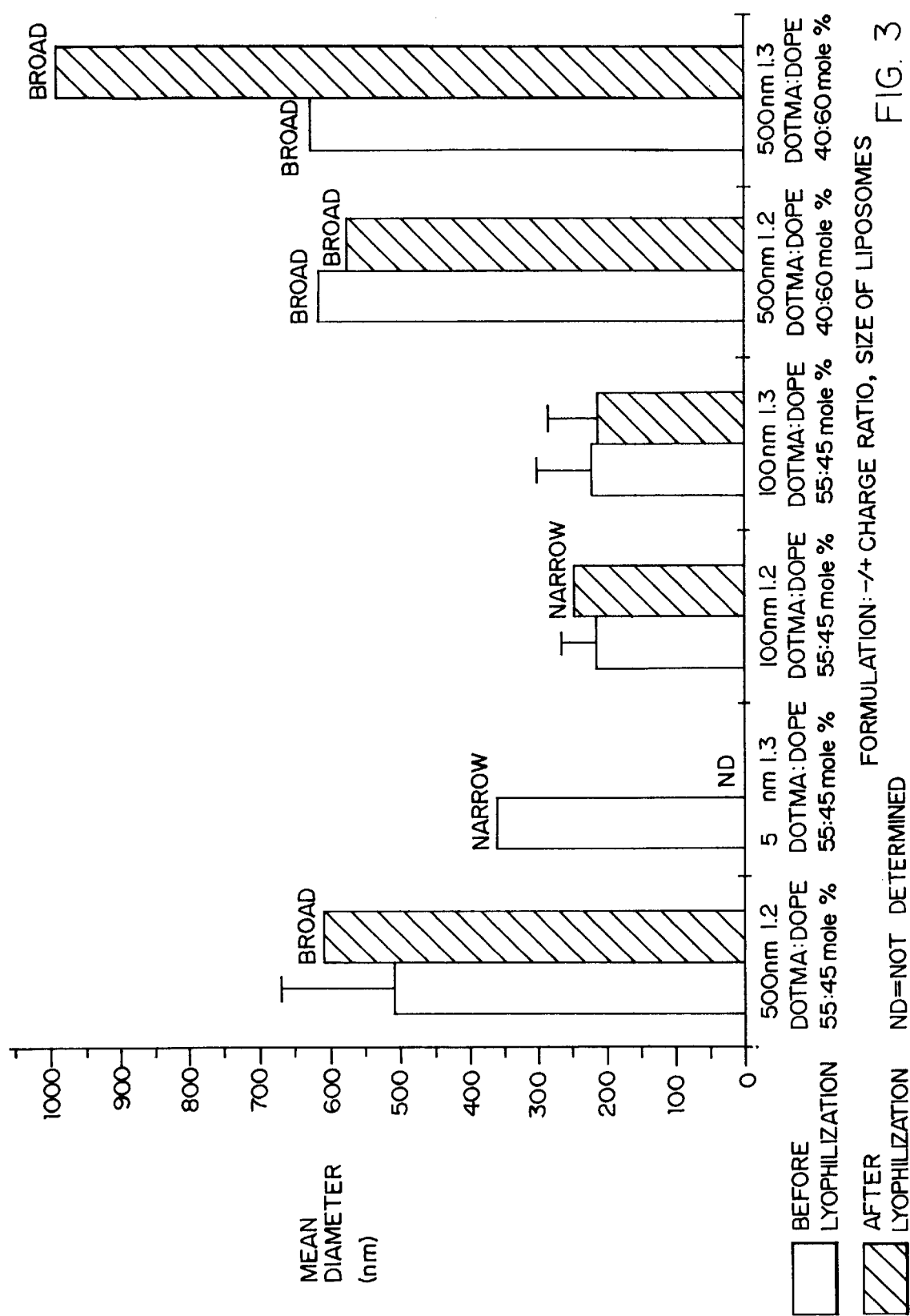
FIG. 3 shows the particle size distribution for various lipid-polynucleotide complexes before and after lyophilization.

FIG. 3 shows the particle size distribution before and after lyophillization for various lipid-pDNA complexes protected with 10% lactose. Lyophillization had little effect on particle size distribution regardless of the lipid composition or charge ratio.

FIG. 4 compares the zeta potential of lipid-pDNA complexes in the presence and absence of cryoprotectant. The presence of 10% lactose had substantially no effect on the zeta potential, except at a charge ratio of 1:1.

FIG. 5 is a graphical representation of gel electrophoresis results comparing lipid-pDNA complexes before and after lyophillization. Migration of the bands was generally unaffected following lyophillization and rehydration. This indicates the complexation between the lipid and the pDNA was not affected by the addition of 10% lactose.

Figure 6:
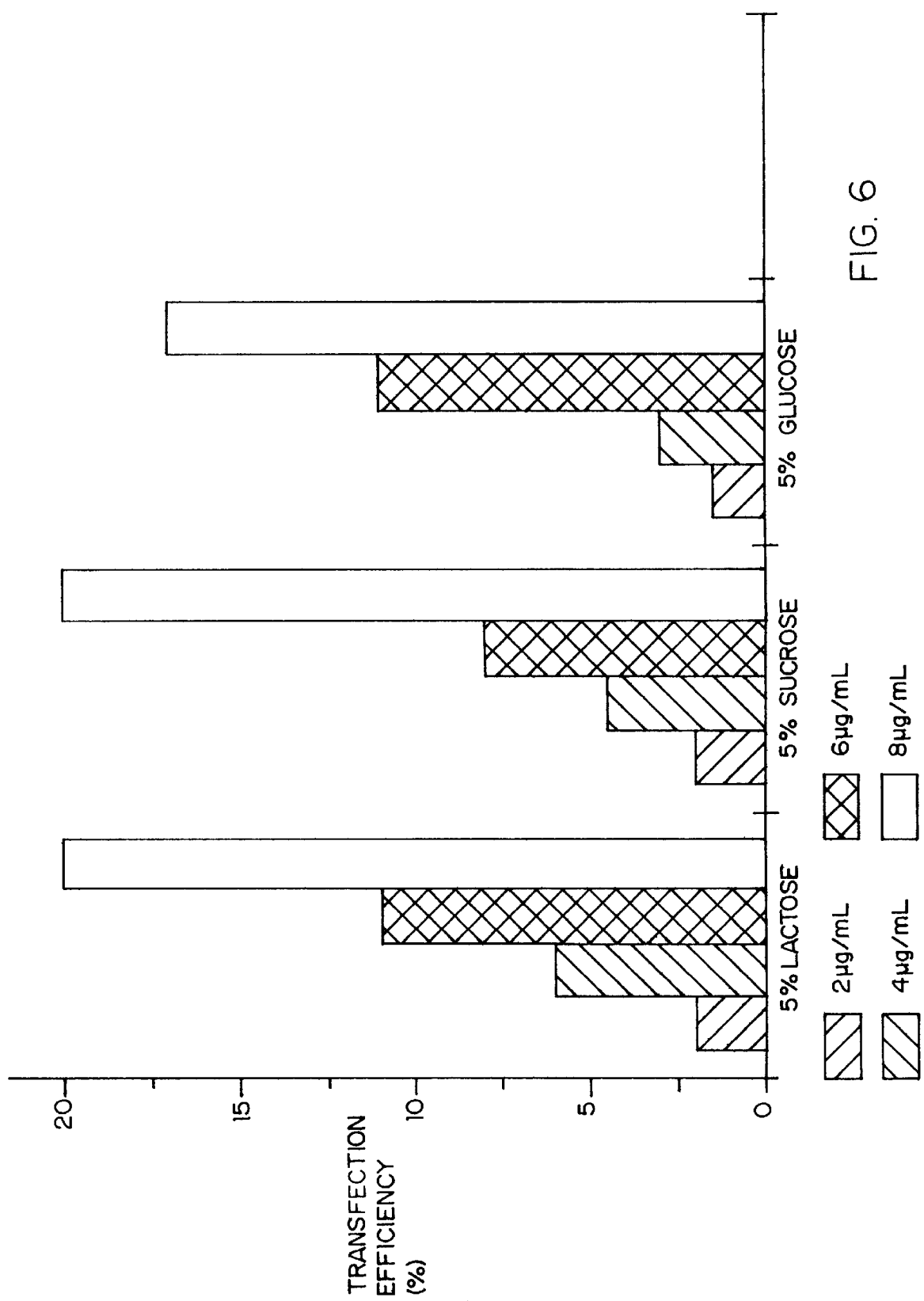
FIGS. 6 and 7 show dose response curves of transfection efficiency comparing lyophillized and non-lyophillized lipid-polynucleotide complexes.
Figure 7:
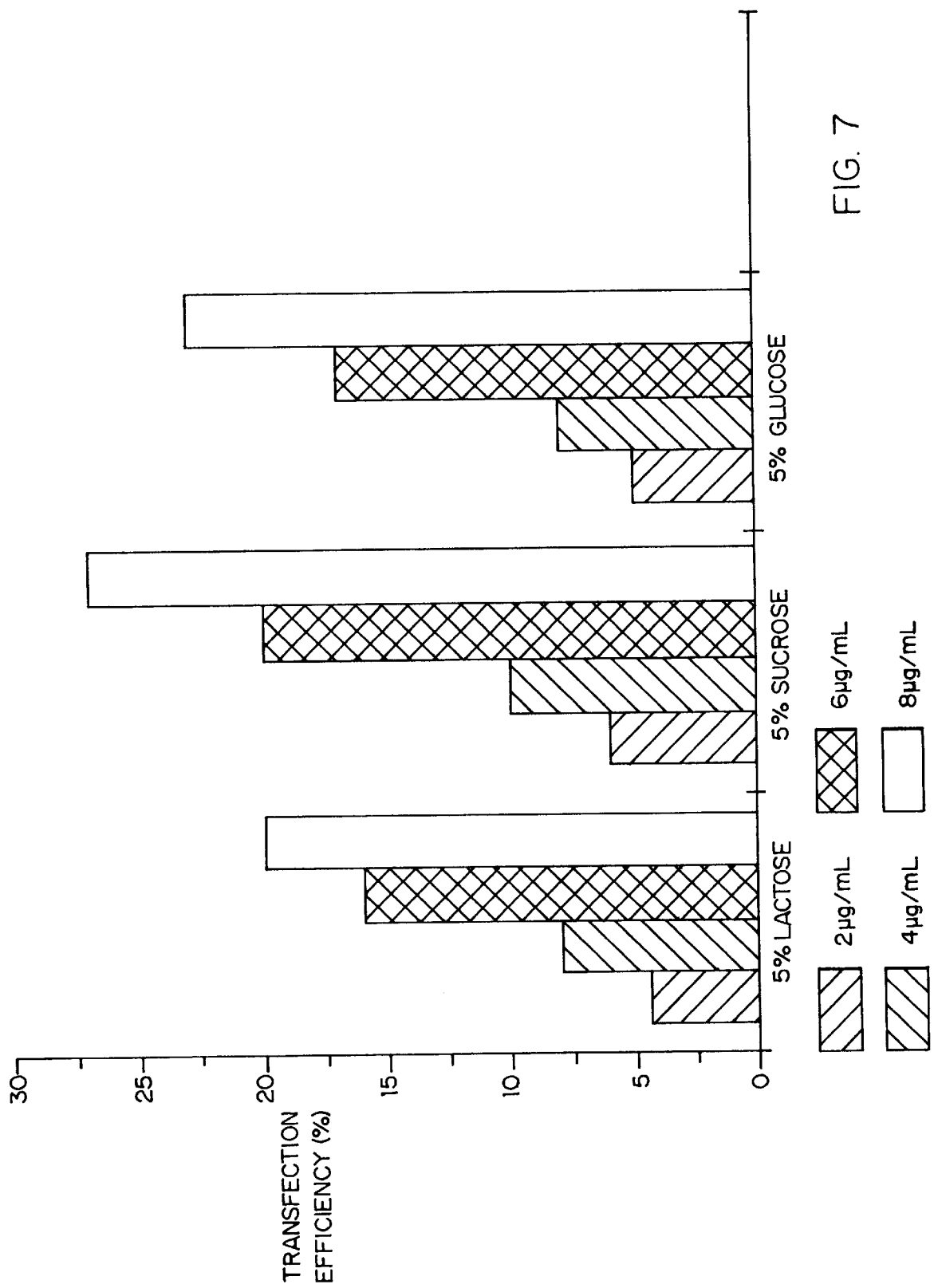
Figure 8:
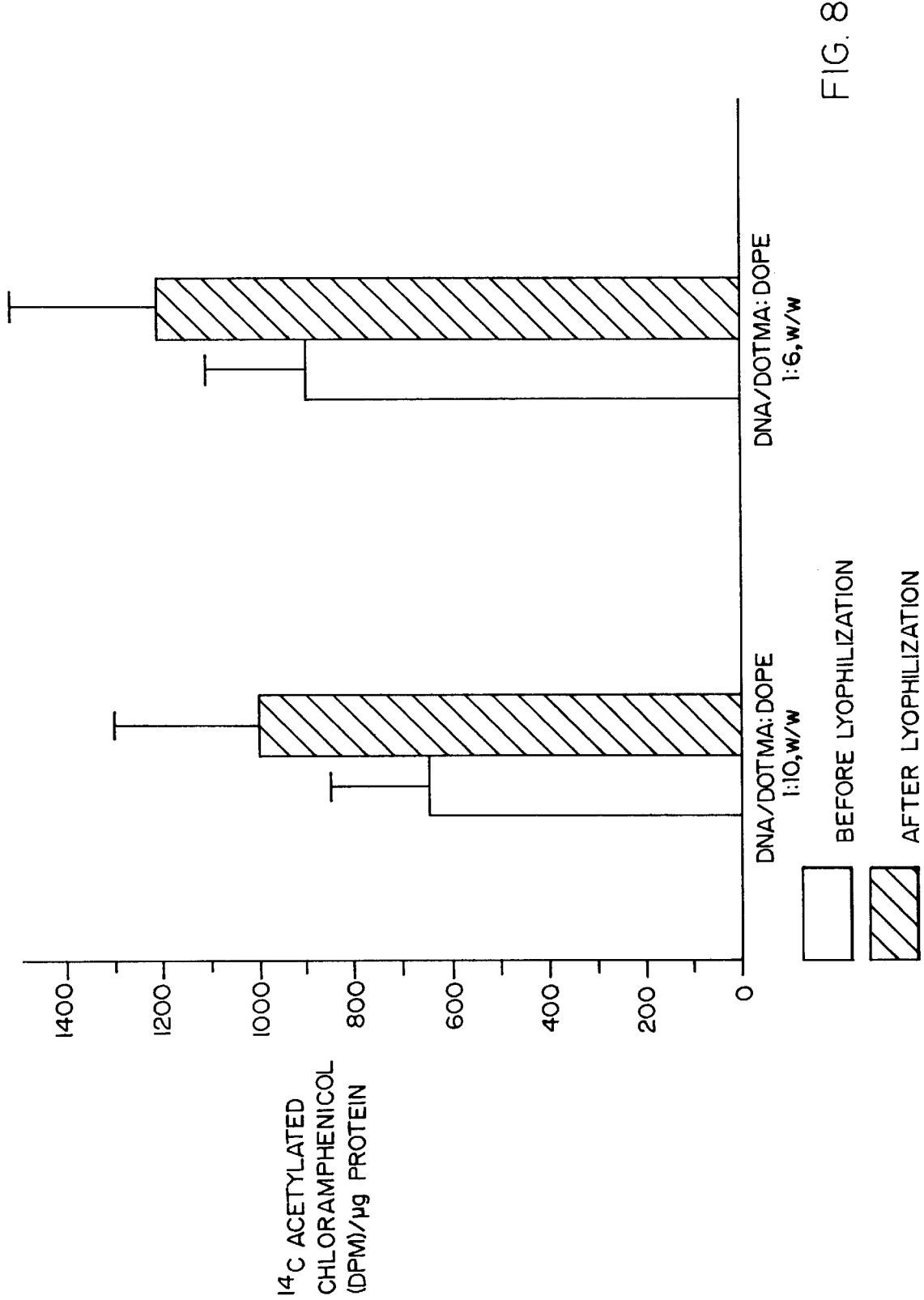
FIGS. 8–10 show the effect of lyophilization on transfection efficiency for lipid-polynucleotide complexes.
Figure 9:
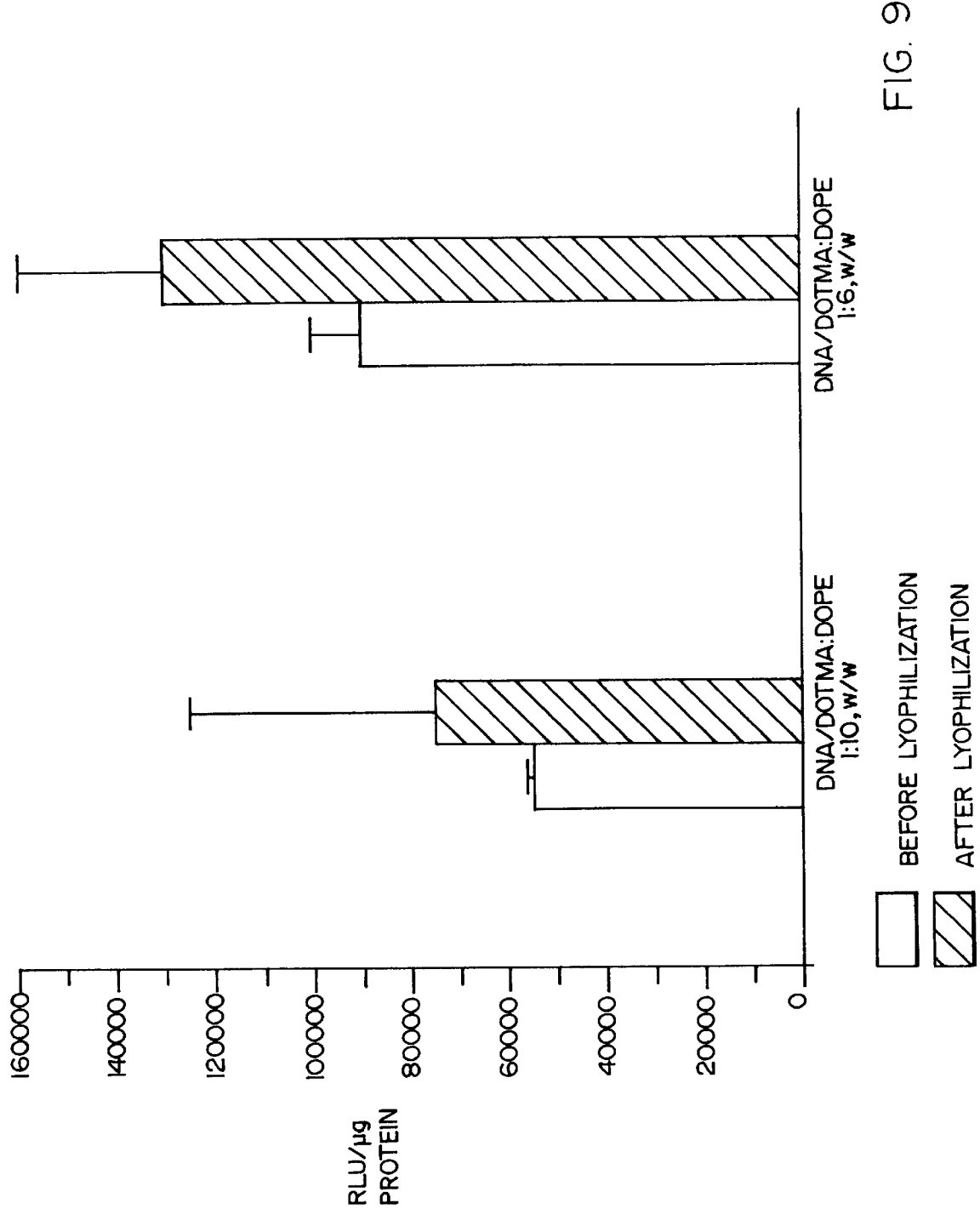
Figure 10:
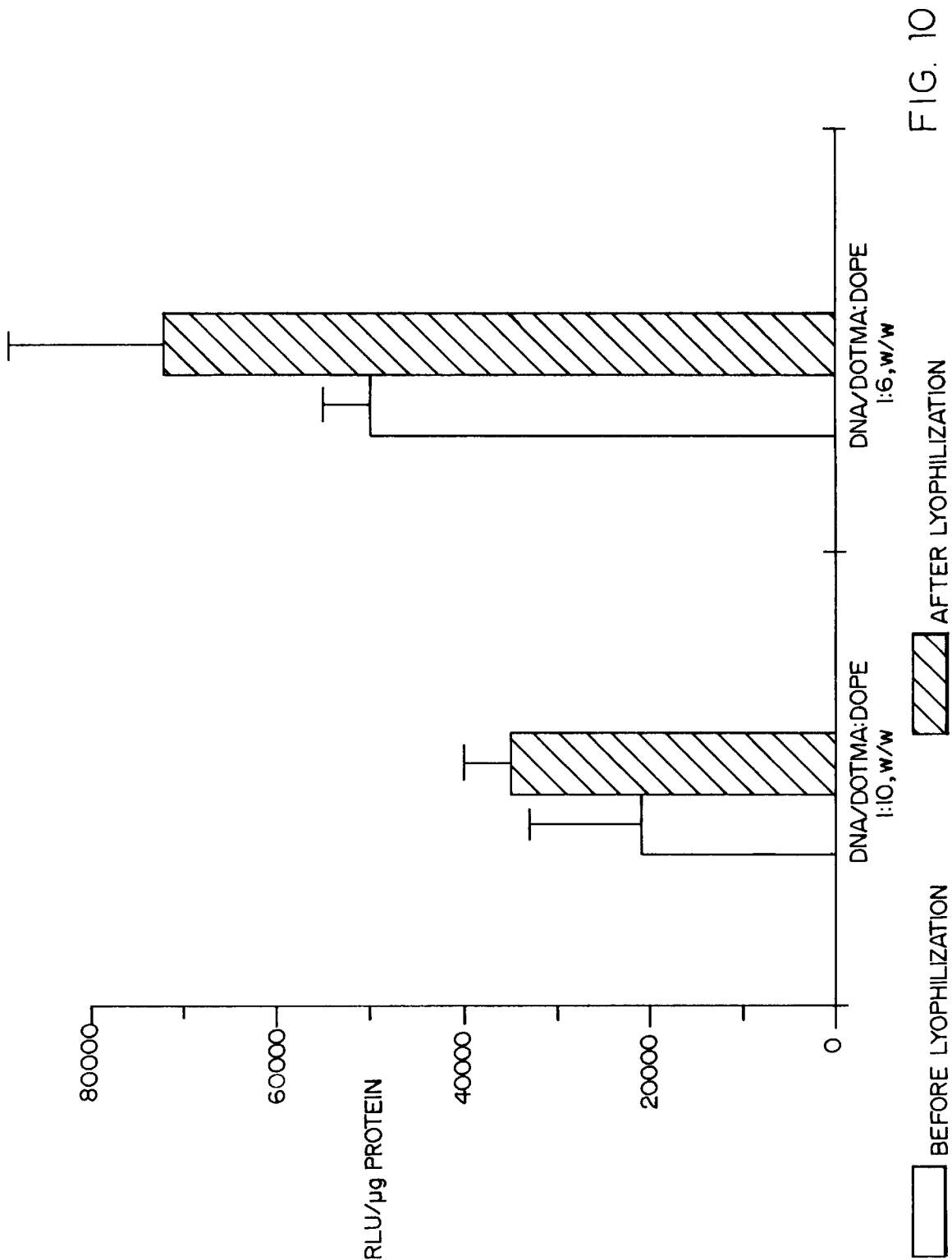

FIGS. 6 and 7 show dose response curves of transfection efficiency comparing lyophillized and non-lyophillized lipid-pDNA complexes protected with 5% lactose, sucrose or glucose. At each pDNA concentration and for each cryoprotectant, transfection efficiency was either unaffected or improved by lyophillization. FIGS. 8–10 show the effect of lyophilization on transfection efficiency for lipid-pDNA complexes: FIG. 8 shows transfer of CMV-CAT at pDNA:DOTMA/DOPE ratios of 1:10 and 1:6 in $C_2 C_{12}$ cells; FIG. 9 shows transfer of CMV— gal at pDNA:DOTMA/DOPE ratios of 1:10 and 1:6 in $C_2 C_{12}$ cells; and FIG. 10 shows transfer of CMV— gal at pDNA:DOTMA/DOPE ratios of 1:10 and 1:6 in HepG2 cells. In each case transfection efficiency was improved by lyophillization.

Figure 11:
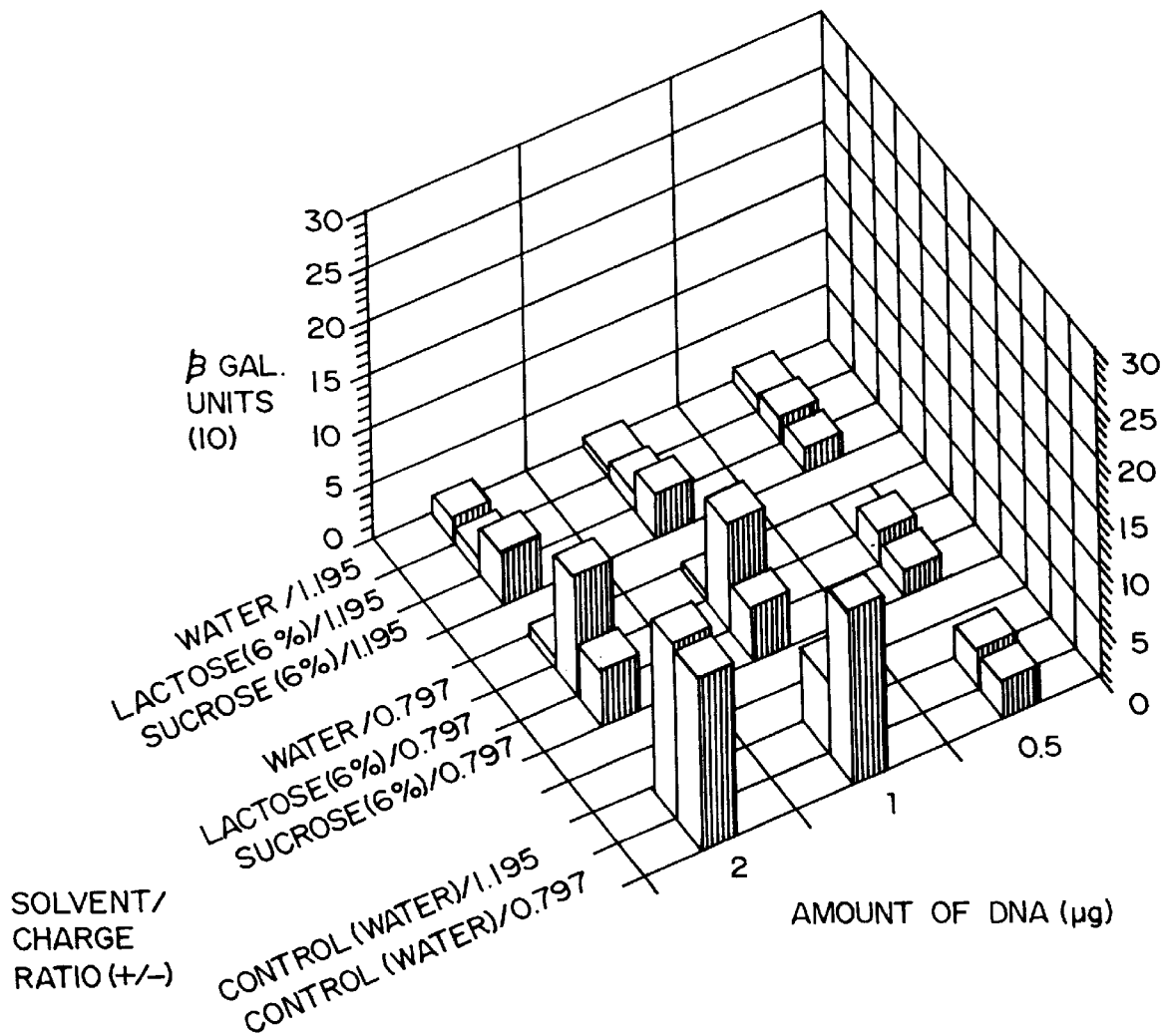
FIGS. 11–13 illustrate the effect of time on the transfection efficiency of lyophillized lipid-polynucleotide complexes.
Figure 12:
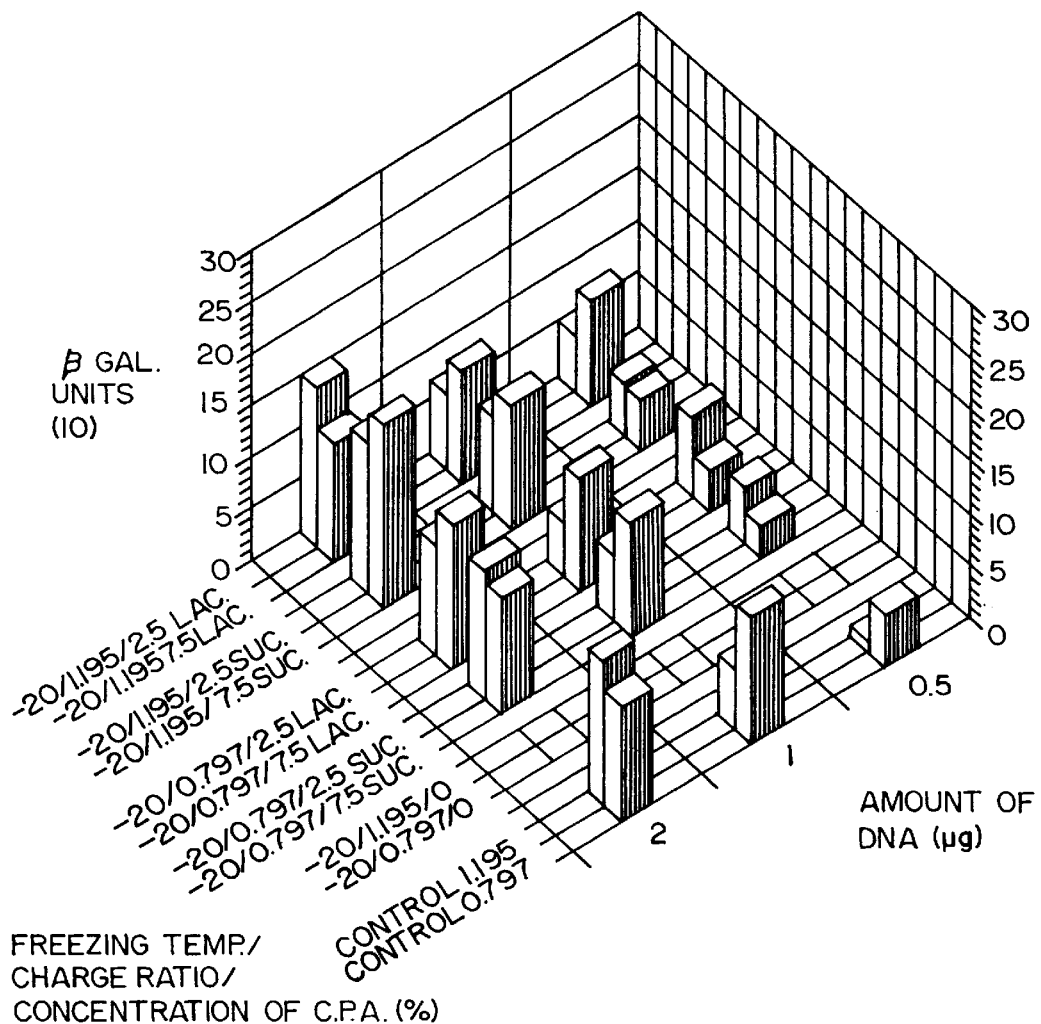
Figure 13:
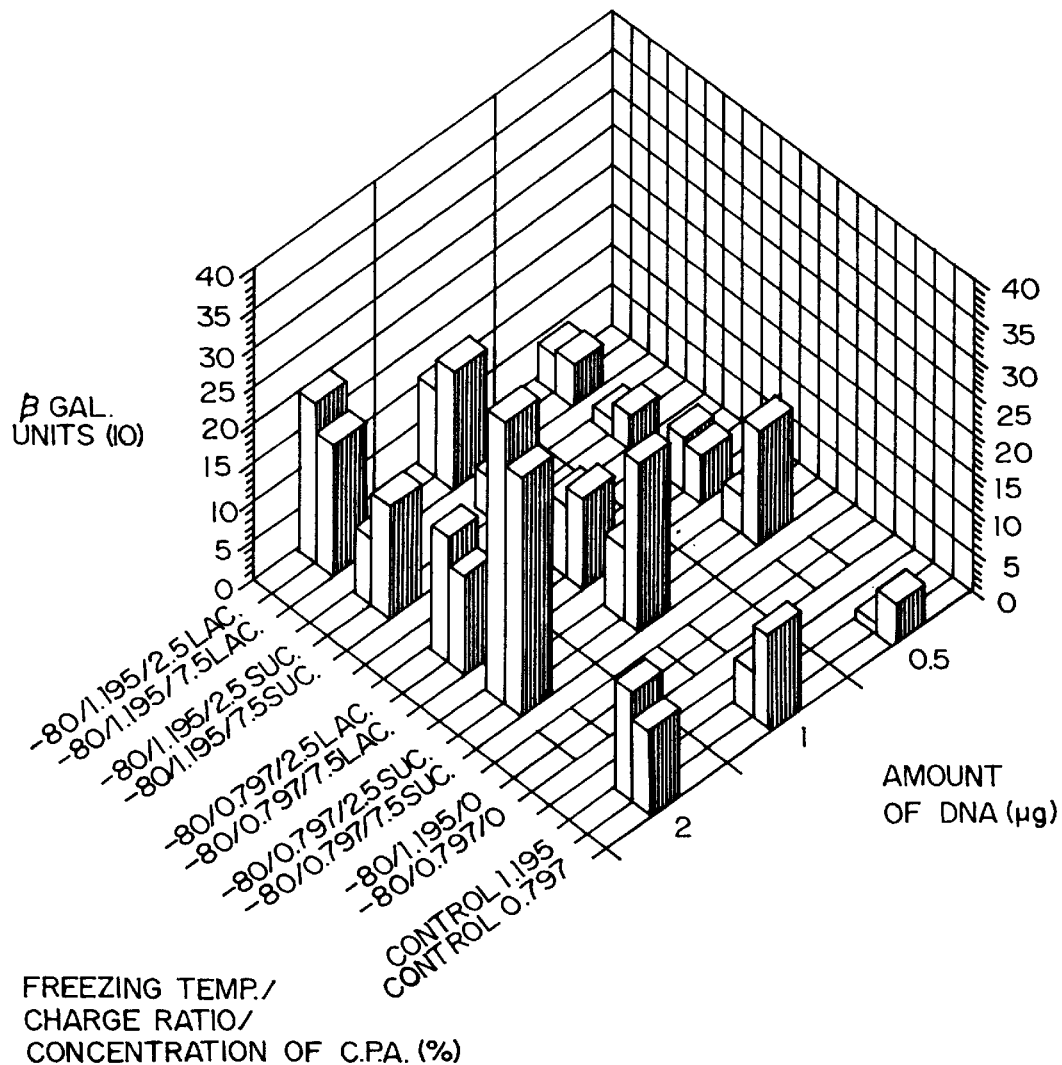
Figure 14:
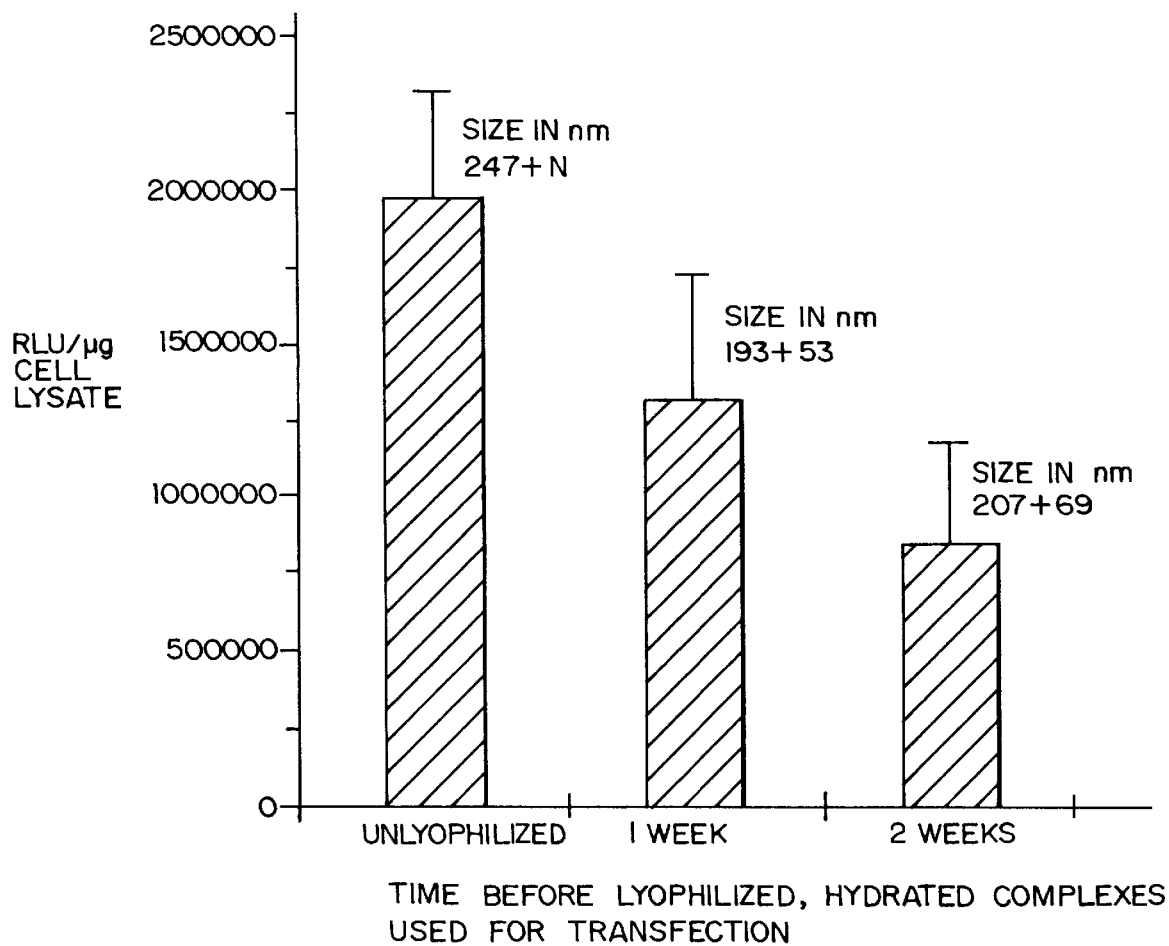
FIG. 14 illustrates the effect of time on the transfection efficiency of rehydrated lipid-polynucleotide complexes.

FIGS. 11–13 show the transfection efficiency of stored DDAB:DOPE-DNA lyophilized complexes prepared at various conditions. Storage of the lyophillized lipid-pDNA did not decrease the transfection efficiency and some cases activity increased. In contrast, FIG. 14 shows the effect of storage time on the activity of rehydrated lipid-pDNA complexes. Transfection efficiency fell over a two week period. This indicates the DNA compositions are stable only when in a lyophillized condition.

Other useful DNA complexes may be prepared as follows:

1. A gramicidin S-pDNA complex is formed with DNA encoding the luciferase gene. At room temperature, 20 μg of pDNA is diluted in 300 μl of 30 mM Tris HCL pH 8.5 in a polystyrene tube. Gramicidin S is diluted in Tris HCL 30 mM ph 8.5 buffer to a concentration of 2 mg/ml from a stock solution of 20 mg/ml in dimethyl sulfoxide. The diluted gramicidin S (20 μl/40 μg) is added to the DNA and quickly mixed. Then 175 μl of liposomes (equivalent to 175 nmoles of lipids) are slowly added with gentle mixing to the DNA-gramicidin S mixture. Lactose is added to a final concentration of 225 mM and the material placed in a vial. The formulation is frozen in a dry-ice ethanol bath and then lyophillized to produce a dry cake. The dry cake may be stored at 4° C. and rehydrated to original volume.

Figure 15:
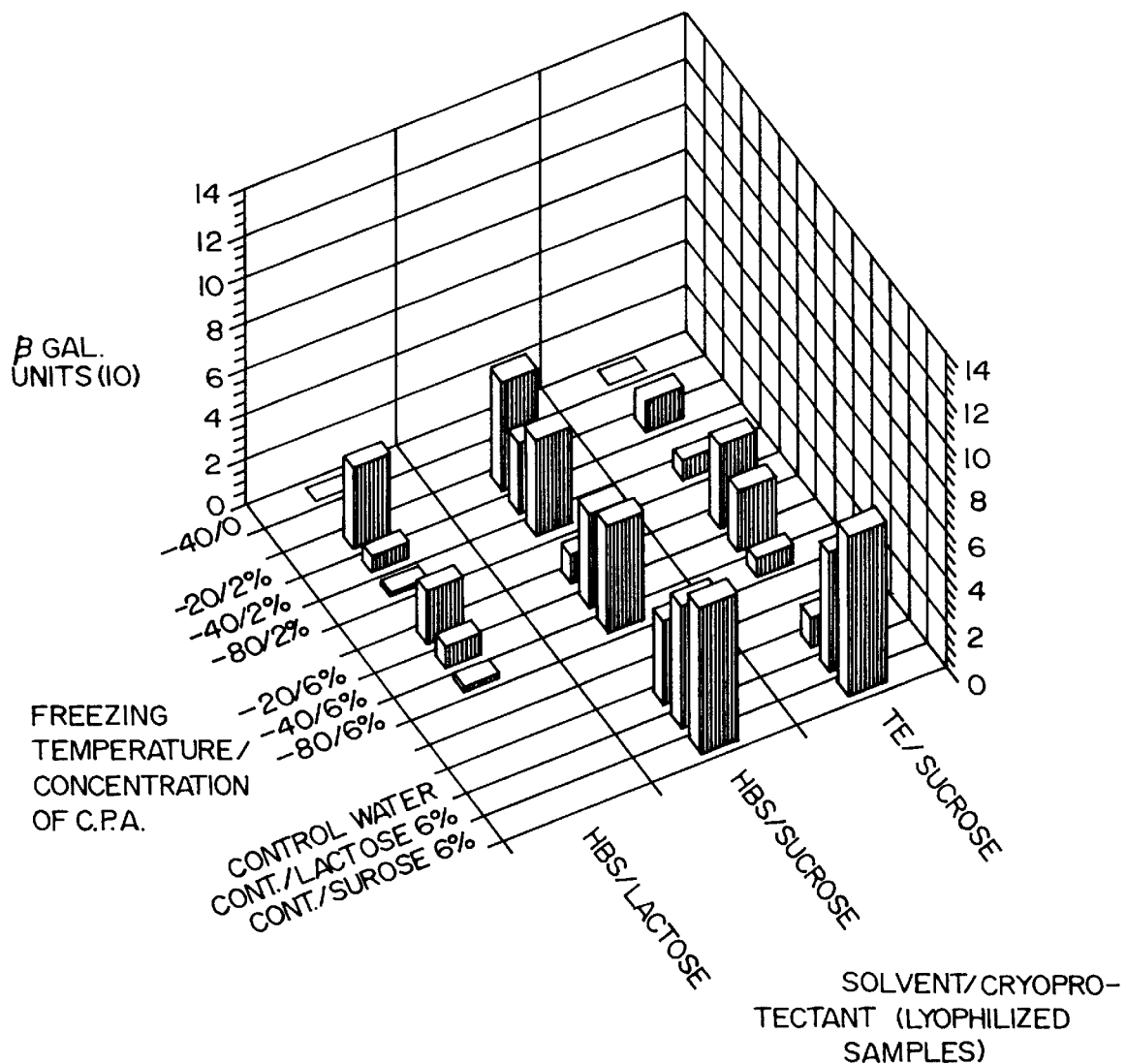
FIG. 15 illustrates transfection using lyophilized dendrimer-polynucleotide complexes.

2. A dendrimer-pDNA complex is formed with DNA encoding the luciferase gene. 6μg of pDNA is diluted in 330 μl of 10 mM Hepes pH 7.3 in a polystyrene tube. The polycation sixth generation starburst dendrimer (2–160 μg) is diluted in Tris HCL 170 of HBS and added dropwise to the DNA and then gently mixed. Lactose is added to a final concentration of 225 mM and the material placed in a vial. The formulation is frozen in a dry-ice ethanol bath and then lyophillized to produce a dry cake. The dry cake may be stored at 4° C. and rehydrated to original volume. FIG. 15 shows expression in cells transfected using a β-gal-dendrimer complex cryoprotected with lactose or sucrose and lyophilized at various temperatures.

Figure 16:
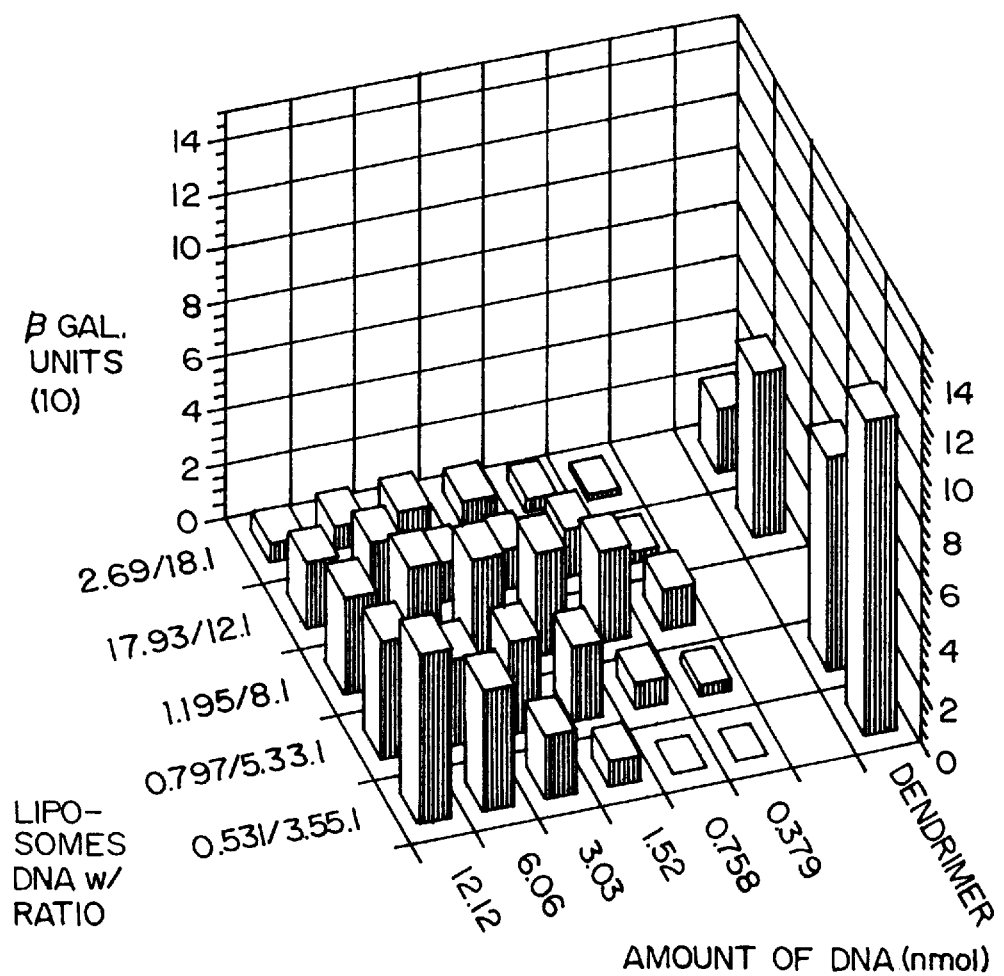
FIGS. 16–17 illustrate transfection using other lipid-polynucleotide complexes.
Figure 17:
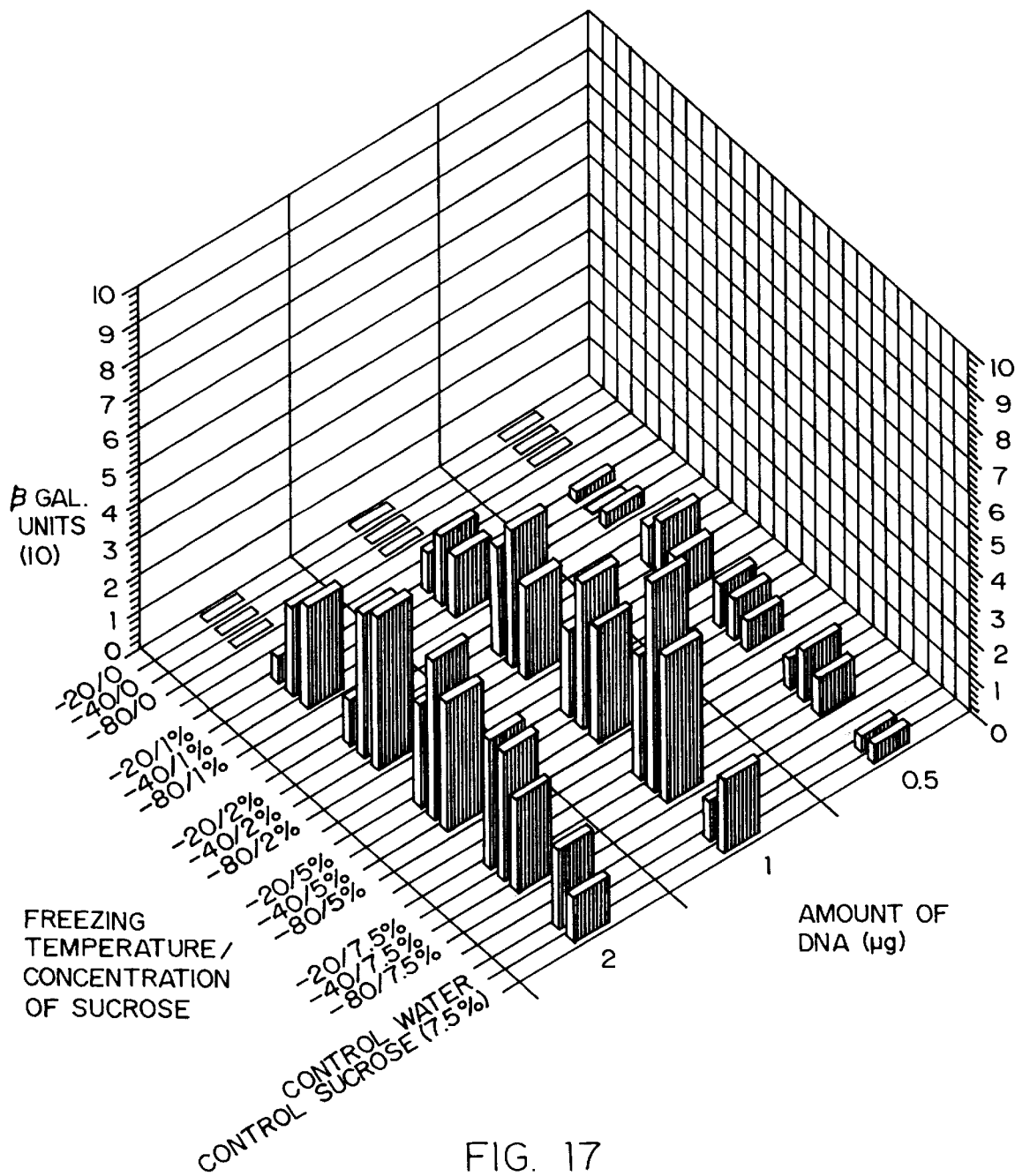

Using methods similar to those above, other useful lipid-polynucleotide complexes may be cryoprotected and lyophilized. FIG. 16 illustrates transfection using lyophilized complexes of β-gal associated with a 1:2 molar ratio of dimethyldioctadecylammonium bromide [DDAB]:dioleoyl phosphatidylethanolamine [DOPE] at varied charge ratios and varied doses. The complexes were cryoprotected at a pDNA:lactose weight ratio of 1:15. FIG. 17 shows transfection using lyophilized complexes of β-gal associated with a 1:1 molar ratio of [DOTAP]:dioleoyl phosphatidylethanolamine [DOPE] lyophilized with various concentrations of sucrose and frozen at various temperatures.

In other embodiments, other cryoprotectants may be used at similar concentration to the above examples. By lyophilizing in the minimal concentration of cryoprotectant, the formulations can be lyophilized and then rehydrated in a lesser volume to concentrate polynucleotide complex. The formulations may also include buffers that can be removed during lyophillization allows concentration of the preparation and subsequent rehydration to isotonicity. Suitable volatile buffers include triethanolamine-acetate, triethanolamine-carbonate, ammonium acetate, ammonium carbonate and other at concentrations from about 0.01M to about 2M. For example, a polynucleotide complex in a 1.25% sucrose solution and a 100 mM ammonium triethanolamine carbonate may be lyophilized and then rehydrated to ⅛ the original volume, maintaining the isotonicity of the rehydrated solution and concentrating the polynucleotide complex 8-fold.

Cationic lipids are useful in forming complexes to be cryoprotected and lyophilized. Conventional cationic lipids suitable for the practice of the invention include phosphatidylethanolamine [PE], dioleyloxy phosphatidylethanolamine [DOPE], n-[1-(2,3-dioleyloxy)propyl]-N,N,N-trimethylammonium chloride [DOTMA], dioleoylphosphatidylcholine [DOPC], 2,3-dioleyloxy-N-[2-(sperminecarboxyamido)ethyl]-N,N-dimethyl-1-propanaminium trifluoroacetate [DOSPA], [DOTAP], [DOGG], dimethyidioctadecylammonium bromide [DDAB], cetyidimethylethylammonium bromide [CDAB], cetyltrimethylethylammonium bromide [CTAB], monooleoyl-glycerol [MOG], 1,2 dimyristyloxypropyl-3-dimehtyl-hydroxyethyl ammonium bromide [DMRIE], 1,2 dimyristoyl-sn-glycero-3-ethylphosphocholine [EDMPC], 1,2 dioleoyl-sn-glycero-3-ethylphosphocholine [EDOPC], 1 palmitoyl, 2 myristoyl-sn-glycero-3-ethylphosphocholine [EPMPC], cholesterol [Chol] and cationic bile salts. Other useful cationic lipids may be prepared in the following manners.

Figure 19:
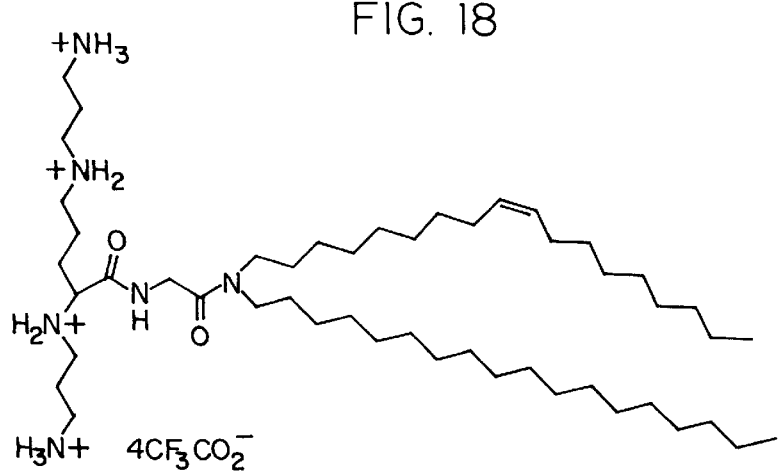
FIGS. 19–31 show various cationic lipids useful in forming lipid:polynucleotide complexes for lyophilization.

Spermine-5-carboxyglycine (N'-stearyl-N'-oleyl) amide tetratrifluoroacetic acid salt (JK-75) FIG. 19.

A p-nitrophenyl oleinate ester was prepared by a standard method. This active ester coupled with octadecylamine to give N-octadecyl oleic amide. Reduction of this amid by lithium aluminum hydride formed N-stearyl N-oleyl amine. A mixture of N-stearyl N-oleyl amine, N-butoxycarbonylglycine p-nitrophenyl ester, and triethylamine in dichloromethane was stirred at room temperature under argon for 24 h. The organic solution was extracted three times with 0.5M sodium carbonate, followed by water, and then dried over sodium sulfate. The solvent was removed under reduced pressure, and the residue was purified by a silica gel flash column to give N-t-butoxycarbonylglycine (N'-stearyl-N'-oleyl) amide. This compound was deprotected by trifluoroacetic acid to give glycine (N'-stearyl-N'-oleyl) amide, which was then treated with tetra-t-butoxycarbonylspermine-5-carboxylic acid (prepared by the cyanoethylation of ornitine, followed by a hydrogenation and protection with Boc-on), dicyclohexylcarbodiimide and N-hudroxysuccinimide in dichloromethane in dark at room temperature under argon for 48 h. The solvent was removed under reduced pressure, and the residue was purified by a silica gel column. The desired compound was then deprotected in trifluoroacetic acid at room temperature for 10 min. The excess of acid was removed under vacuum to yield the spermine-5-carboxyglycine (N'-stearyl-N'-oleyl) amide tetra trifluoroacetic acid salt, as a light yellow wax. $^1$H NMR (300 Mhz, CD$_3$OD) δ5.20 (m, 2 H), 4.01 (s, 2 H), 3.87 (t, 1 H), 3.19–2.90 (m, 16 H), 2.01–1.27 (m, 21 H), 1.15 (broad s, 56 H), 0.76 (t, 6 H). LSIMS (NBA): m/e 805.8 for M$^{4+}$(C$_{49}$H$_{104}$N$_6$O$_2$)–3 H$^+$.

Figure 20:
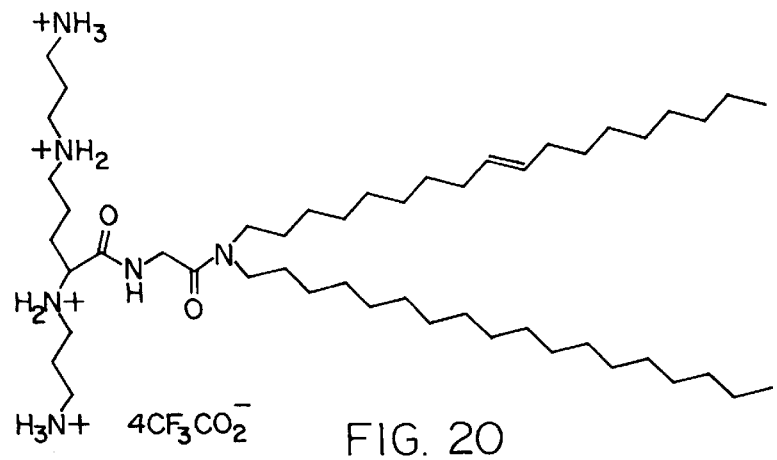

Spermine-5-carboxyglycine (N'-stearyl-N'-elaidyl) amide tetratrifluoroacetic acid salt (JK-76). FIG. 20.

Produced in a similar manner, by substituting for the appropriate starting material. $^1$H NMR (300 MHz, CD$_3$OD): δ5.24 (m, 2 H), 4.01 (s, 2 H), 3.87 (t, 1 H), 3.14–2.90 (m, 16 H), 2.01–1.21 (m, 21 H), 1.15 (broad s, 56 H), 0.76 (t, 6 H). LSIMS (NBA): m/e 805.8 for M$^{4+}$(C$_{49}$H$_{104}$N$_6$O$_2$)–3 H$^+$

Figure 21:
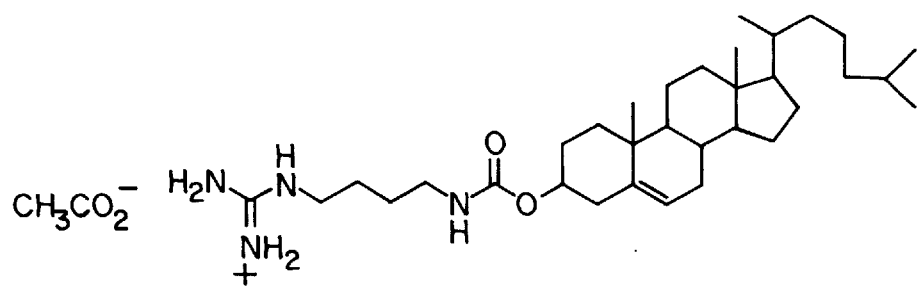

Agmatinyl carboxycholesterol acetic acid salt (AG-Chol) FIG. 21.

Agmatine sulfate (100 mg, 0.438 mmol) was treated by tetramethylamonium hydroxide (158 mg, 0.876 mmol) in methanol (15 ml) for 1 h. The solvent was removed under reduced pressure. A suspension solution of the residue and cholesteryl chloroformate (197 mg, 0.438 mmol) in DMF (15 ml) was stirred at room temperature for 3 days. Filtration of the reaction mixture gave the crude product as a light yellow solid, which was purified by a silica gel column using chloroform-methanol-acetic acid (10:2:1) as eluent to yield the agmatinyl carboxycholesterol acetic acid salt as a white solid. $^1$H NMR (300 MHz, CD$_3$OD): δ5.27 (broad s, 1 H), 4.65 (broad m, 1 H), 3.06 (t, 2 H), 2.99 (t, 2 H), 2.21 (broad d, 2 H), 1.95–0.65 (m, 31 H), 1.80 (s, 4 H), 0.91 (s, 3 H), 0.82 (d, 3 H), 0.76 (s, 3 H), 0.74 (s, 3 H), 0.59 (s, 3 H). LSIMS (NBA): m/e 543.4 for M+(C$_{33}$H$_{59}$N$_4$O$_2$).

Figure 22:
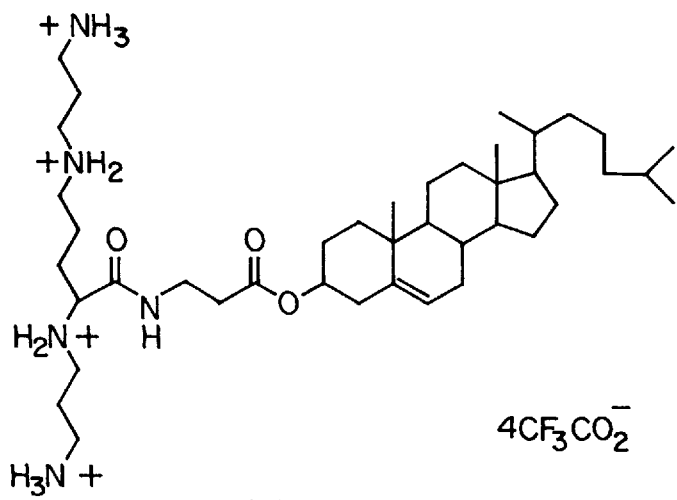

Spermine-5-carboxy-β-alanine cholesteryl ester tetratrifluoroacetic acid salt (CAS) FIG. 22.

A solution of cholesteryl β-alanine ester (0.2 mmol), prepared with standard procedure, in dichloromethane (dry, 2 ml) was added into a solution of tetra-t-butoxycarbonylspermine-5-carboxylic acid N-hydroxysuccinimide ester (0.155 mmol) and 4-methylmorpholine (0.4 ml) in dichloromethane (5 ml). The reaction mixture was stirred at room temperature under argon for 6 days. The solvent was removed under reduced pressure, and the residue was purified by a silica gel column using ethanol-dichloromethane (1:20) as eluent to give the desired product as a light yellow oil. This compound was treated with trifluoroacetic acid (0.5 ml) at room temperature under argon for 10 min. The excess trifluoroacetic acid was removed under reduced pressure to give spermine-5-carboxy-β-alanine cholesteryl ester tetratrifluoroacetic acid salt as a white solid. $^1$H NMR (300 MHz, CDCl$_3$): δ5.38 (m, 1 H), 4.60 (m, 1 H), 3.90 (t, J=6.16, 1 H), 3.54 (m, 2 H), 3.04 (m, 10 H), 2.58 (t, J=6.71, 2 H), 2.33 (d, J=6.58, 2 H), 2.15–0.98 (m, 36 H), 1.04 (s, 3 H), 0.93 (d, J=6.46, 3 H), 0.87 (d, J=6.59, 6 H), 0.70 (s, 3 H). LSIMS (NBA): m/e 687.5 for M$^{4+}$(C$_{41}$H$_{80}$N$_5$O$_3$)–3 H$^+$.

Figure 23:
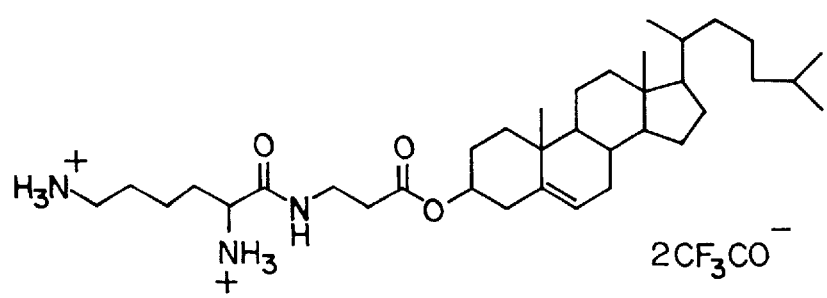

2,6-Diaminohexanoeyl β-alanine cholesteryl ester bistrifluoroacetic acid salt (CAL) FIG. 23.

Produced in a manner similar to CAS, by substituting for the appropriate starting material. $^1$H NMR (300 MHz, CDCl$_3$): δ8.10–7.62 (m, 7 H), 5.38 (broad s, 1 H), 4.60 (broad s, 1 H), 4.08 (broad s, 1 H), 3.40 (broad s, 4 H), 3.02 (broad s, 4 H), 2.50 (broad s, 2 H), 2.26 (broad s, 2 H), 2.04–0.98 (m, 28 H), 1.04 (s, 3 H), 0.93 (d, J=6.46, 3 H), 0.88 (d, J=6.59, 6 H), 0.74 (s, 3 H). LSIMS (NBA): m/e 586.5 for M$^{2+}$(C$_{36}$H$_{65}$N$_3$O$_3$)–H$^+$.

Figure 24:
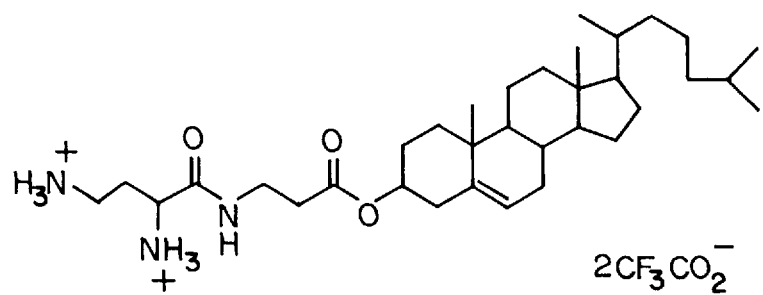

2,4-Diaminobutyroyl β-alanine cholesteryl ester bistrifluoroacetic acid salt (CAB) FIG. 24.

Produced in a manner similar to CAS, by substituting for the appropriate starting material. $^1$H NMR (300 MHz, CDCl$_3$): δ8.34–8.06 (m, 7 H), 5.38 (broad s, 1 H), 4.60 (broad s, 1 H), 4.30–3.20 (broad m, 11 H), 2.50–0.98 (m, 36 H), 1.04 (s, 3 H), 0.93 (d, J=6.46, 3 H), 0.88 (d, J=6.59, 6 H), 0.74 (s, 3 H). LSIMS (NBA): m/e 558.5 for M$^{2+}$ (C$_{34}$H$_{61}$N$_3$O$_3$)–H$^+$.

Figure 25:
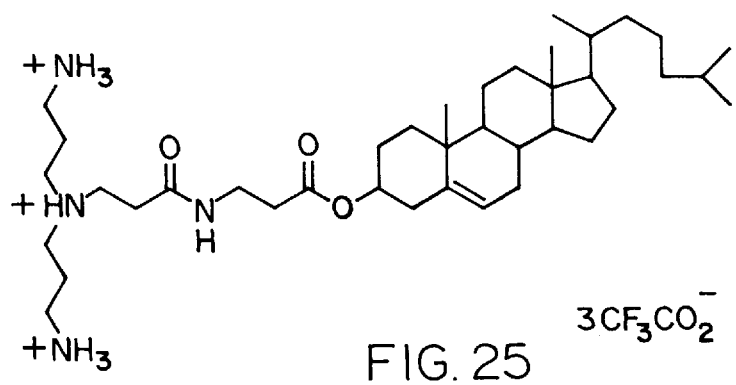

N,N-Bis(3-aminopropyl)-3-aminopropionyl β-alanine cholesteryl ester tristrifluoroacetic acid salt (CASD) FIG. 25.

Cyanoethylation of the β-alanine with acrylnitrile in the presence of 1,4-diazabicyclo [2.2.2] octane at 90° C. for 15 h gave the N,N-bis(2-cyanoethyl)-3-aminopropionic acid. Hydrogenation of the N,N-bis(2-cyanoethyl)-3-aminopropionic acid in ethanol-water (1:1) using Raney nickel as catalyst yielded the N,N-bis(3-aminoethyl)-3-aminopropionic acid. The amino groups of this compound was protected by 2-(t-butoxycarbonyloxylmino)-2-phenylacetonitrile in acetone-water (4:1) to give N,N-bis(t-butoxycarbonyl-3-animoethyl)-3-aminopropionic acid. This compound was activated by chloroacetonitrile and triethylamine to form cyanomethyl N,N-bis(t-butoxycarbonyl-3-animoethyl)-3-aminopropionate. A solution of the cyanomethyl ester and cholesteryl β-alanine ester in chloromethane was stirred in dark at room temperature under argon for 10 days. The solvent was removed under reduced pressure, and the residue was purified by a silica gel column using methanol-chloroform (1:10) as eluent to yield the N,N-bis (t-butoxycarbonyl-3-aminoethyl)-3-aminopropionoyl β-alanine cholesteryl ester. Treatment of this compound with trifluoroacetic acid formed N,N-bis(3-aminopropyl)-3-aminopropionoyl β-alanine cholesteryl ester tristrifluoroacetic acid salt. $^1$H NMR (300 MHz, CD$_3$OD-CDCl$_3$ 1:1): δ8.13 (broad s, 3 H), 5.78 (broad s, 3 H), 5.38 (broad s, 1 H), 5.18 (s, 1 H), 4.74 (s, 1 H), 4.60 (broad s, 1 H), 3.54–3.04 (m, 10 H), 2.80 (t, J=6.60, 2 H), 2.73 (t, J=6.54, 2 H), 2.53 (t, J=6.42, 2 H), 2.32 (d, J=6.58, 2 H), 2.15–0.98 (m, 30 H), 1.04 (s, 3 H), 0.91 (d, J=6.42, 3 H), 0.86 (d, J=6.58, 6 H), 0.70 (s, 3 H). LSIMS (NBA): m/e 643.5 for M$^{3+}$ (C$_{39}$H$_{73}$N$_4$O$_3$)–2H$^+$.

Figure 26:
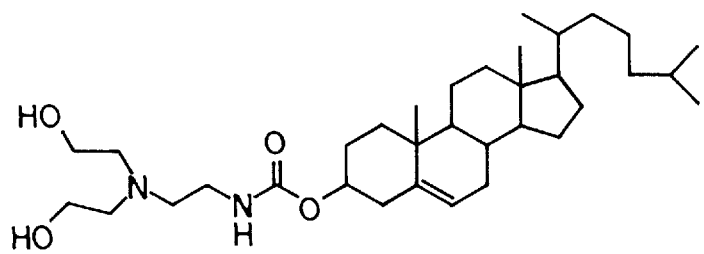

[N,N-Bis(2-hydroxyethyl)-2-aminoethyl] aminocarboxy cholesteryl ester (JK-154) FIG. 26.

A solution of cholesteryl chloroformate (0.676 g, 1.51 mmol) and ethelenediamine (4 ml) in chloroform (10 ml) was stirred in dark at room temperature under argon for 16 h. The solvent and excess of ethylendiamine were removed under reduced pressure, and the residue was purified by a silica gel column using CH$_3$OH—CHCl$_3$ (NH$_3$) (v/v, 0–20 %) as eluent to give ethylendiamine cholesterylcarboxymonoamide as a white solid. A mixture of this compound (80 mg, 0.17 mmol), 2-hydroxyethylbromide (2 ml) and triethylamine (2 ml) was stirred in dark at room temperature under argon for 14 days. The excess of triethylamine and 2-hydroxyethylbromide were removed under reduced pressure, and the residue was purified by a silica gel column using CH$_3$OH—CHCl$_3$ (v/v, 1:3) as eluent to give the 2-[N,N-Bis(2-hydroxyethyl)aminoethyl]amino carboxy cholesteryl ester as a white solid. $^1$H NMR (300 MHz, CDCl$_3$): δLSIMS (NBA): m/e 643.5 for M$^{3+}$(C$_{39}$H$_{73}$N$_4$O$_3$) −2H$^+$.

Carnitine ester lipids

Figure 27:
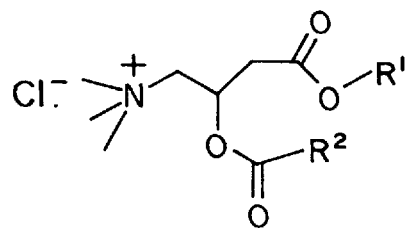

Carnitine lipids are synthesized by acylating the hydroxy group of L-carnitine by standard methods to create the monoacyl carnitine. The carboxy group of the carnitine is modified with a second acyl chain to make a phospholipid analog with a single quarternary ammonium cationic group. The other carnitine stereoisomers D- and D,L- are suitable, but the L-form is preferred. The acyl chains are between 2 and 30 carbons and may be saturated or unsaturated, with from 1 to 6 unsaturated groups in either the cis or trans configuration. The acyl chains may also contain iso forms. A preferred form comprises the oleoyl group, a chain 18 carbons long with a cis unsaturated bond at C$_9$. This generic carnitine ester is shown in FIG. 27. Presently preferred carnitine esters follow.

Stearyl carnitine ester

A solution of DL-carnitine hydrochloride (1.0 g, 5.05 mmol) and sodium hydroxide (0.303 g, 7.58 mmol) in ethanol (15 ml) was stirred at room temperature for 2 h. The formed white precipitate (NaCl) was removed by filtration, and the solvent was evaporated under reduced pressure to give a white solid, carnitine inner salt. A suspension of the carnitine inner salt and 1 -iodooctadecane (2.31 g, 6.06 mmol) in DMF-dioxane (3:5, 40 ml) was heated with an oil-bath at 120° C. under Ar$_2$ for 4 h. The solvent was removed by rotavapor and vacuum, and the residue was chromatographied with silica gel column using CH$_3$OH—CH$_3$Cl as eluant to give 2.22 g (81%) of stearyl carnitine ester as a white solid: $^1$H NMR (CDCl$_3$) δ4.79 (m, 1 H), 4.43 (d, J=5.3, 1 H), 4.09 (t, J=6.9, 2 H), 4.03 (d, J=13.0, 1 H), 3.67 (dd, J=10.3, 13.3, 1 H), 3.51 (s, 9 H), 2.79 (dd, J=5.7, 17.0, 1 H), 2.66 (dd, J=7.0, 17.1, 1 H), 1.80–1.60 (m, 4 H), 1.26 (broad s, 28 H), 0.88 (t, J=6.6, 3 H). LSIMS (NBA): m/e 414.4 for C$_{25}$H$_{52}$NO$_3$ (cation).

Palmityl carnitine ester

With the procedure used for the preparation of stearyl carnitine ester, 0.77 g (4.77 mmol) of carnitine inner salt and 2.52 g (7.15 mmol) of 1-iodohexadecane to give 1.59 g (65 %) of palmityl carnitine ester as a white solid: $^1$H NMR (CDCl$_3$) δ4.78 (m, 1 H), 4.44 (d, J=5.4, 1 H), 4.09 (t, J=6.9, 2 H), 3.65 (dd, J=10.2, 13.3, 1 H), 3.58 (d, J=5.1, 1 H), 3.51 (broad s, 9 H), 2.80 (dd, J=5.7, 17.2, 1 H), 2.66 (dd, J=7.1, 17.1, 1 H), 1.65 (broad m, 4 H), 1.26 (broad s, 24 H), 0.88 (t, J=0.66, 3 H). LSIMS (NBA): m/e 386.2 for C$_{23}$H$_{48}$NO$_3$ (cation).

Myristyl carnitine ester

With the procedure used for the preparation of stearyl carnitine ester, 0.77 g (4.77 mmol) of carnitine inner salt and 2.31 g (7.15 mmol) of 1-iodotetradecane gave 1.70 (74%) of myristyl carnitine ester as a white solid: $^1$H NMR (CDCl$_3$) δ4.79 (m, 1 H), 4.43 (d, J=5.3, 1 H), 4.09 (t, J=6.9, 2 H), 4.03 (d, J=13.0, 1 H), 3.67 (dd, J=10.3, 13.3, 1 H), 3.51 (s, 9 H), 2.79 (dd, J=5.7, 17.0, 1 H), 2.66 (dd, J=7.0, 17.1, 1 H), 1.80–1.60 (m, 4 H), 1.26 (broad s, 20 H), 0.88 (t, J=6.6, 3 H). LSIMS (NBA): m/e 358.1 for C$_{21}$H$_{44}$NO$_3$ (cation).

Figure 28:
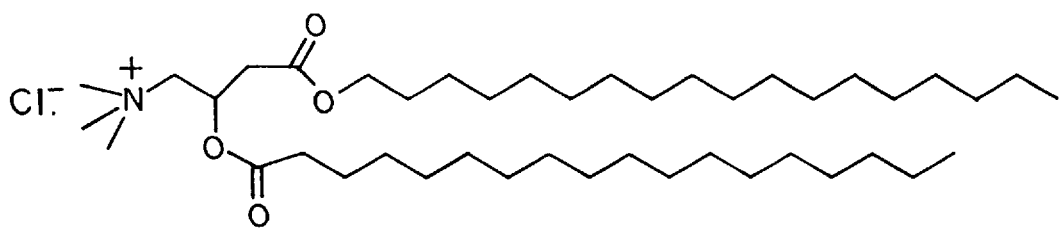

Stearyl stearoyl carnitine ester chloride salt (SSCE)
FIG. 28.

A solution of DL-carnitine hydrochloride (1.0 g, 5.05 mmol) and sodium hydroxide (0.303 g, 7.58 mmol) in ethanol (15 ml) was stirred at room temperature for 2 h. The formed white precipitate (NaCl) was removed by filtration, and the solvent was evaporated under reduced pressure to give a white solid, carnitine inner salt. A suspension of the carnitine inner salt and 1-iodooctadecane (2.31 g, 6.06 mmol) in DMF-dioxane (3:5, 40 ml) was heated with an oil-bath at 120° C. under argon for 4 h. The solvent was removed under reduced pressure, and the residue was purified by a silica gel column using CH$_3$OH—CH$_3$Cl (v/v, 0–10%) as eluent to give the stearyl carnitine ester as a white solid. A solution of a fresh prepared stearic anhydride (1.94 g, 3.52 mmol), stearyl carnitine ester (0.953 g, 1.76 mmol) and 4-dimethylaminopyridine (0.429 g, 3.52 mmol) in CH$_3$Cl (dry, 15 ml) was stirred at room temperature under argon for four days. The solvent was removed under reduced pressure, and the residue was washed twice by cold diethyl ether. The solid was chromatographied on a silica gel column using MeOH—CHCl$_3$ (v/v, 1:5) as eluent to give the stearyl stearoyl carnitine ester iodide. The iodide was exchanged by chloride with an anion exchange column to give the stearyl stearoyl carnitine ester chloride as a white solid. $^1$H NMR (300 MHz, CDCl$_3$) δ5.67 (q, 1 H), 4.32 (d, 1 H), 4.07 (m, 3 H), 3.51 (s, 9 H), 2.82 (t, 2 H), 2.33 (t, 2 H), 1.59 (broad m, 4 H), 1.25 (broad s, 58 H), 0.88 (t, 6 H). LSIMS (NBA): m/e 680.6 for M$^+$(C$_{43}$H$_{86}$NO$_4$). Anal. Calcd for C$_{43}$H$_{86}$ClNO$_4$.H$_2$O: C, 70.30; H, 12.07; N, 1.91. Found: C, 70.08; H, 12.24; N, 1.75.

L-Stearyl Stearoyl Carnitine Ester (L-SSCE) was prepared with the same procedure using L-carnitine as starting material. Analytical data are same as DL-SSCE.

Figure 29:
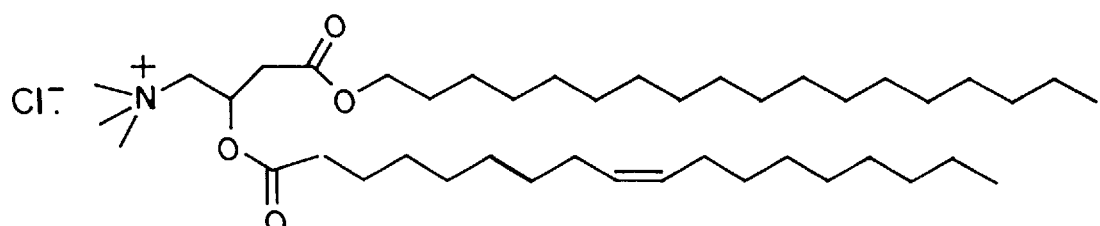

Stearyl oleoyl carnitine ester chloride (SOCE)
FIG. 29.

Prepared in a manner similar to SSCE, by substituting the appropriate starting material.

$^1$H NMR (300 MHz, CDCl$_3$): δ5.67 (q, 1 H), 5.35 (m, 2 H), 4.32 (d, 1 H), 4.08 (m, 3 H), 3.48 (s, 9 H), 2.83 (dd, 2 H), 2.34 (dd, 2 H), 2.02 (broad m, 4 H), 1.26 (broad m, 54 H), 0.88 (t, 6 H). LSIMS (NBA): m/e 678.7 for M+(C$_{43}$H$_{84}$NO$_4$). Anal. Calcd for C$_{43}$H$_{84}$ClNO$_4$.H$_2$O: C, 70.50; H, 11.83; N, 1.91. Found: C, 70.77; H, 12.83; N, 1.93.

Figure 30:
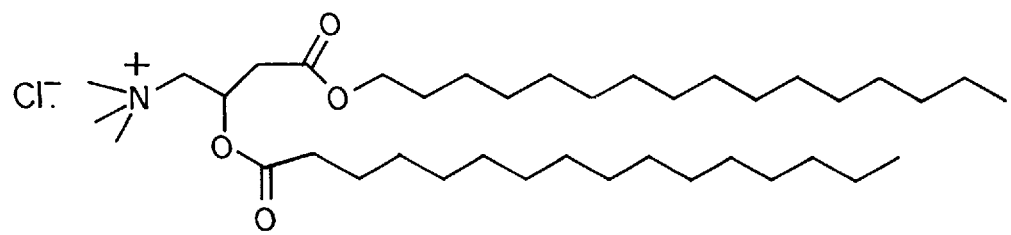

Palmityl palmitoyl carnitine ester chloride (PPCE)
FIG. 30.

Prepared in a manner similar to SSCE, by substituting the appropriate starting material.

$^1$H NMR (300 MHz, CDCl$_3$): δ5.67 (q, 1 H), 4.33 (d, 1 H), 4.07 (m, 3 H), 3.51 (s, 9 H), 2.82 (t, 2 H), 2.33 (t, 2 H), 1.59 (broad m, 4 H), 1.25 (broad s, 58 H), 0.99 (t, 6 H). LSIMS (NBA): m/e 680.6 for M+(C$_{43}$H$_{78}$NO$_4$). Anal. Calcd for C$_{39}$H$_{78}$ClNO$_4$.H$_2$O: C, 69.04; H, 11.88; N, 2.06. Found: C, 69.31; H, 11.97; N, 2.37.

Figure 31:
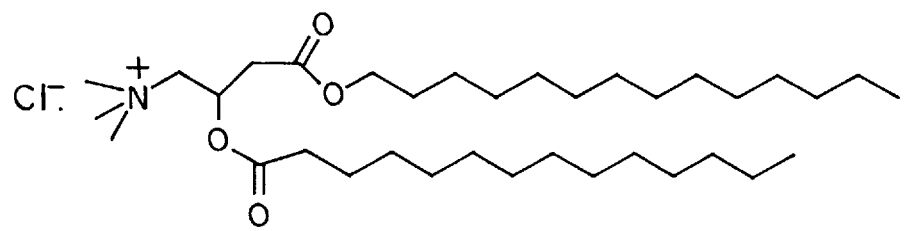

Myristyl myristoyl carnitine ester chloride (MMCE)
FIG. 31.

Prepared in a manner similar to SSCE, by substituting the appropriate starting material.

$^1$H NMR (300 MHz, CDCl$_3$): δ5.67 (q, 1 H), 4.32 (d, 1 H), 4.07 (m, 3 H), 3.50 (s, 9 H), 2.82 (t, 2 H), 2.33 (t, 2 H), 1.61 (broad m, 4 H), 1.26 (broad s, 42 H), 0.88 (t, 6 H). LSIMS (NBA): m/e 568.6.7 for M+(C$_{35}$H$_{70}$NO$_4$). Anal. Calcd for C$_{35}$H$_{70}$ClNO$_4$.1/2H$_2$O:C, 68.53; H, 11.67; N, 2.28. Found: C, 68.08; H, 11.80; N, 2.21.

L-Myristyl myristoyl carnitine ester chloride (L-MMCE) was prepared with the same procedure using L-carnitine as starting material. Analytical data are same as DL-MMCE. m.p. 157° C. (decomposed).

These results demonstrate a number of the benefits exhibited by lyophilized polynucleotide complexes. The freeze-drying process does not substantially effect the physicochemical properties of the polynucleotide complexes yet confer stability over protracted periods of time. The formulations allow preparation of high concentrations of complex. For cationic lipids at least, lyophilization with certain cryoprotectants followed by rehydration results in improved transfection efficiencies compared to non-lyophilized controls. It is believed that the process stabilizes the polynucleotide-cation interaction, generating complexes of defined particle size following rehydration.

Dry Powder Formulations

Lyophillized polynucleotide complexes may be sieved or milled to produce dry powder formulations (DPF). The powder may be used to generate a powder aerosol for delivering the polynucleotide to the lung. A current limitation of aerosol delivery is that high concentrations of DNA must be used in order to achieve sufficient gene transfer. At these concentrations, the polynucleotide complexes aggregate. The DPF permits use of high concentrations of polynucleotide. The powder is diluted when dispersed into the lung so that risk of aggregation is minimized. Once in contact with the lung tissue, the powder will rehydrate and regain its activity.

Figure 18:
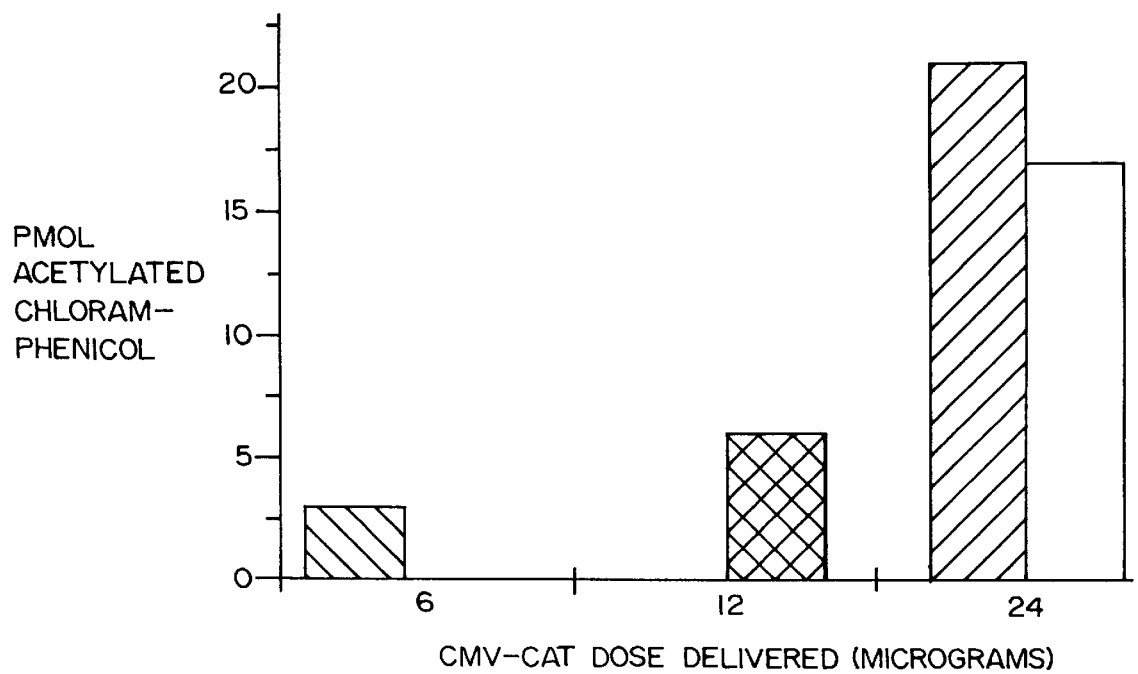
FIG. 18 shows expression of genetic information transferred using a dry powder formulation of a lyophilized polynucleotide complex.

In a first example, plasmid CMV-CAT DNA was complexed as described above with a DOTMA:DOPE lipid formulation at a ratio of 1:10 (w/w). As a control, naked pCMV-CAT may be cryoprotected. The cryoprotectant mannitol was added at pDNA:mannitol ratios of 1:100 and 1:500 (w/w). The formulations were lyophillized at a product eutect temperature of 30° C. to form a dry cake and retained under vacuum. Control instillation formulations were rehydrated to provide physicochemical and transfective comparison to the DPFs. The lyophillized product was sieved using a brass U.S.A. Standard 38 $\mu$m Sieve Apparatus in a dry glove box. The complex powder was sieved into crystalline lactose (Pharmatose ) to produce a 1:6 (w/w) powder:Pharmatose concentration. Pharmatose acts as a carrier for the DPF formulations. In other embodiments, a carrier may not be desirable. Resulting exemplary pCMV-CAT concentrations for the DPFs are as follows:

1:0:100 (w/w/w) pDNA:lipid:mannitol—1.41 $\mu$g/mg
1:10:100 (w/w/w) pDNA:lipid:mannitol—1.29 $\mu$g/mg
1:0:500 (w/w/w) pDNA:lipid:mannitol—0.29 $\mu$g/mg
1:10:500 (w/w/w) pDNA:lipid:mannitol—0.28 $\mu$g/mg The DPFs were tested for in vivo activity by treating mice with the formulations and a Pharmatose control, harvesting the lung and trachea and assessing CAT expression. 10 mg of DPF were delivered via direct intratracheal injections using a Penn-Century Delivery device, resulting in approximately 50% delivery. FIG. 18 shows that the CMV-CAT DPF delivered at various doses resulted in CAT expression in the lung cells.

In another example, similar DPFs were produced using a jet milled using a high speed shear mixer. A 1:10:100 (w/w/w) pDNA/lipid/mannitol complex was jet milled at a grinding pressure of 130 psi and a feed rate of 40 mg/ml. The resulting powder had a nearly monodisperse particle size distribution of 80% at 3.2–3.8 $\mu$m as determined by laser light scattering. Electron microscopy revealed that many particles were <1 $\mu$m. Jet milling at a grinding pressure of 80 psi and a feed rate of 700 mg/ml resulted in a nearly monodisperse particle size distribution of 80% at 3.7–4.8 $\mu$m. In comparison, a sieved DPF showed a slight increase in the percentage of particles <10 $\mu$m. Prior to jet milling, the DPF was polydisperse with a particle size distribution of 80% at 5–27 $\mu$m.

Figure 32:
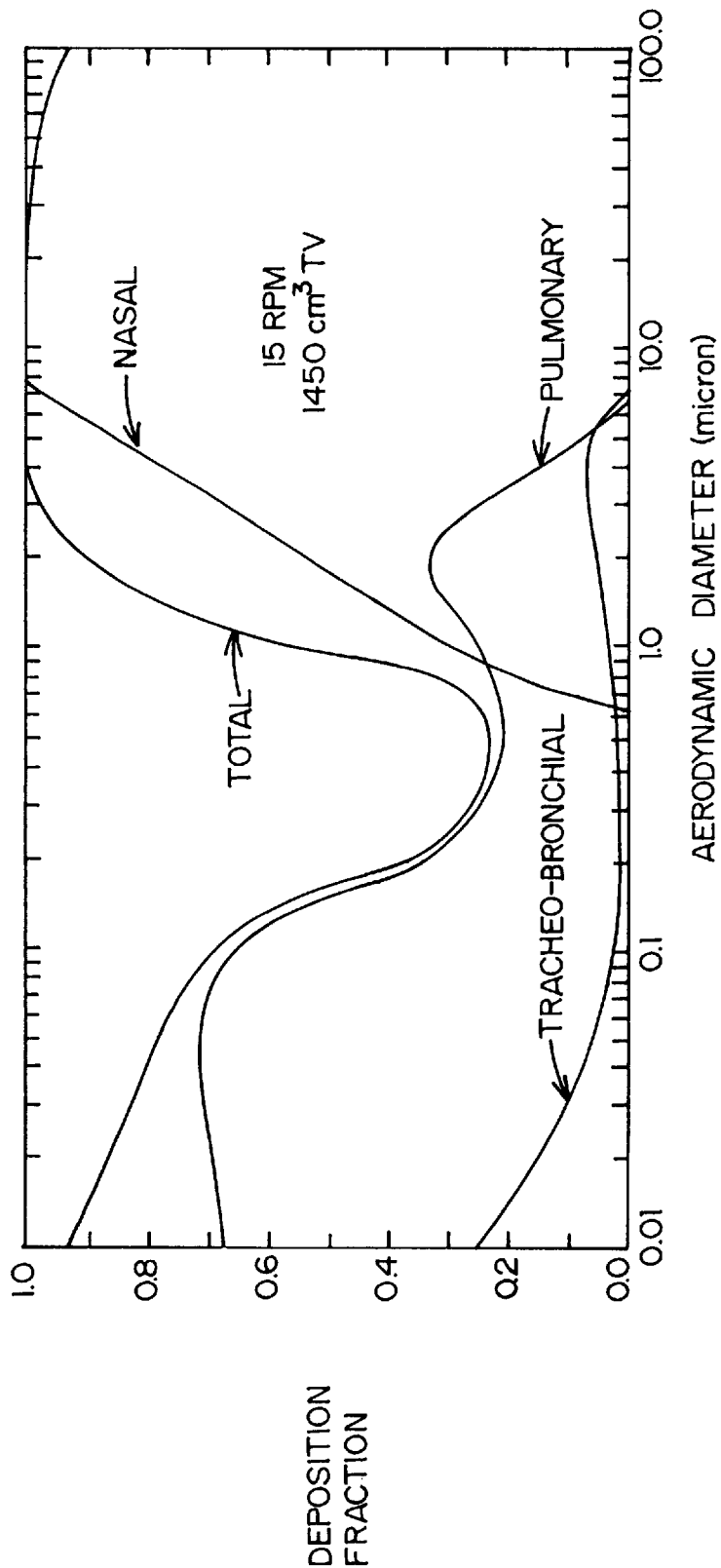
FIG. 32 shows predicted deposition sites in the respiratory tract for various size particles.

DPFs may be used to deliver genes useful in the treatment of a lung disease. For example, complexes formed with DNA encoding for cystic fibrosis transmembrane conductance regulator (CFTR) may be used to treat cystic fibrosis. In similar manner, other lung diseases such as alpha-1-antitrypsin deficiency, asthma, pulmonary embolism, adult respiratory distress syndrome, pulmonary hypertension, chronic obstructive pulmonary disease, lung cancer, pulmonary fibrosis, pulmonary microbial infections, pulmonary pseudomonas infections, pulmonary inflammatory disorders, chronic bronchitis, pulmonary viral infections, respiratory syncitial virus, lung tissue rejection, emphysema and pulmonary allergic disorders could be treated. In preferred embodiments, the average particle size of the DPF is controlled to skew the deposition of the particles in desired region of the respiratory system. Although the deposition of particles is affected by a number of factors, including environmental conditions, particle characteristics, respiratory tract characteristics and breathing pattern characteristics, predictive models are possible. FIG. 32 shows the deposition fraction at various compartments of the respiratory tract for inhaled aerosols as a function of particle size. DPFs should generally have an average particle size of less than about 100 $\mu$m, preferably less than about 10 $\mu$m, and particularly preferably less than about 1 $\mu$m for treatment of the lung.

In other embodiments, DPFs are useful for the treatment of skin diseases. DPFs could be also be formulated as a pill for ingestion or as a suppository allowing for treatment of a wide range of internal or systemic conditions.

What is claimed is:

1. A method for delivering a polynucleotide to a cell comprising the steps of adding a cryoprotectant to a polynucleotide complex, lyophilizing the complex, producing a dry powder formulation from the lyophilized complex, and contacting the cell with the dry powder formulation.

2. The method of claim 1, wherein the step of contacting the cell with the dry powder formulation comprises aerosolizing the powder and delivering it to cells line the respiratory tract.

3. The method of claim 2, wherein the step of producing the dry powder formulation comprises adjusting the average particle size to selectively deliver the aerosolized powder to a desired region of cells lining the respiratory tract.

4. A composition for delivering a polynucleotide to a cell, comprising a lyophilized formulation of a polynucleotide complex and a cryoprotectant in a dry powder formulation.

5. The composition of claim 4, wherein the dry powder formulation has an average particle size which is not greater than about 100 $\mu$m.

6. The composition of claim 5, wherein the average particle size is not greater than about 10 $\mu$m.

7. The composition of claim 6, wherein the average particle size is not greater than about 1 $\mu$m.

8. A method for treating a polynucleotide complex comprising the steps of adding a cryoprotectant to the polynucleotide complex, lyophilizing the polynucleotide complex and producing a dry powder formulation from the lyophilized complex.

9. The method of claim 8, wherein the step of producing a dry powder formulation comprises sieving the lyophilized complex.

10. The method of claim 8, wherein the step of producing a dry powder formulation comprises jet milling the lyophilized complex.

11. The method of claim 8, wherein the step of producing a dry powder formulation comprises producing a powder with an average particle size of not greater than about 100 μm.

12. A method for delivering a polynucleotide to a eukaryotic cell comprising contacting the eukaryotic cell with the composition of claim 4.

13. The method of claim 12 comprising contacting the cell under in vivo conditions.

14. The method of claim 12 comprising contacting the cell under in vitro conditions.

15. The method of claim 13 comprising contacting a mammalian cell.

16. The method of claim 13 comprising contacting a human cell.

17. The method of claim 14 comprising contacting a mammalian cell.

18. The method of claim 14 comprising contacting a human cell.

19. The composition of claim 4, wherein the polynucleotide complex comprises a lipid-polynucleotide complex wherein the lipid is selected from the group consisting of phosphatidylethanolamine (PE), phosphatidyl choline (PC), dioleyloxy phosphatidylethanolamine (DOPE), n-(1-(2,3-dioleyloxy)propyl)-N,N,N-trimethylammonium chloride (DOTMA), dioleoylphosphatidylcholine (DOPC),2,3-dioleyloxy-N-(2-(sperminecarboxyamido)ethyl)-N,N-dimethyl-l-propanaminium trifluoroacetate (DOSPA), (DOTAP), (DOGG), spermine-5-carboxyglycine(N'-stearyl-N'-stearyl)amide tetra-trifluoroacetic acid salt (DOGS), 1,2 dimyristyloxypropyl-3-dimehtyl-hydroxyethyl ammonium bromide (DMRIE), 1,2 dimyristoyl-sn-glycero-3-ethylphosphocholine (EDMPC), 1,2 dioleoyl-sn-glycero-3-ethylphosphocholine (EDOPC), 1 palmitoyl, 2 myristoyl-sn-glycero-3-ethylphosphocholine (EPMPC) dimethyldioctadecylammonium bromide (DDAB), cetyldimethylethylammonium bromide (CDAB), cetyltrimethylethylammonium bromide (CTAB),), monooleoylglycerol (MOG), cholesterol (Chol), cationic bile salts, spermine-5-carboxyglycine (N'-stearyl-N'-oleyl) amide tetratrifluoroacetic acid salt (JK-75), spermine-5-carboxyglycine (N'-stearyl-N'-elaidyl) amide tetratrifluoroacetic acid salt (JK-76), agmatinyl carboxycholesterol acetic acid salt (AG-Chol), spermine-5-carboxy-β-alanine cholesteryl ester tetratrifluoroacetic acid salt (CAS), 2,6-diaminohexanoeyl β-alanine cholesteryl ester bistrifluoroacetic acid salt (CAL), 2,4-diaminobutyroyl β-alanine cholesteryl ester bistrifluoroacetic acid salt (CAB), N,N-bis (3-aminopropyl)-3-aminopropionyl β-alanine cholesteryl ester tristrifluoroacetic acid salt (CASD), (N,N-bis(2-hydroxyethyl)-2-aminoethyl)minocarboxy cholesteryl ester (JK-154), carnitine ester lipids, stearyl carnitine ester, myristyl carnitine ester, stearyl stearoyl carnitine ester chloride salt (SSCE), L-stearyl stearoyl carnitine ester (L-SSCE), stearyl oleoyl carnitine ester chloride (SOCE), palmityl palimitoyl carnitine ester chloride (PPCE), myristyl myristoyl carnitine ester chloride (MMCE) and L-myristyl myristoyl carnitine ester chloride (L-MMCE).

* * * * *

UNITED STATES PATENT AND TRADEMARK OFFICE
CERTIFICATE OF CORRECTION

PATENT NO. : 5,811,406
DATED : September 22, 1998
INVENTOR(S) : Francis C. Szoka, Jr., et al.

It is certified that error appears in the above-indentified patent and that said Letters Patent is hereby corrected as shown below:

In column 6, line 36, delete "[DOGG]" and insert therefor --[DOGS]--.

In column 6, line 37, delete "cetyidimethylethylammonium" and insert therefor --cetyldimethylethylammonium".

In column 6, line 40, delete "dimehty" and insert therefor --dimethyl--.

In column 6, line 52, delete "amid" and insert therefor --amide--.

In column 12, line 44, delete "line" and insert therefor --lining--.

In column 13, line 32, delete "(DOGG)" and insert therefor --(DOGS)--.

In column 14, line 2, delete "dimehtyl" and insert therefor --dimethyl--.

Signed and Sealed this

Thirtieth Day of November, 1999

Attest:

Q. TODD DICKINSON

Attesting Officer

Acting Commissioner of Patents and Trademarks